United States Patent [19]

Harris et al.

[11] Patent Number: 5,650,096
[45] Date of Patent: Jul. 22, 1997

[54] CATIONIC AMPHIPHILES FOR INTRACELLULAR DELIVERY OF THERAPEUTIC MOLECULES

[75] Inventors: David J. Harris, Lexington; Edward R. Lee, Quincy; Craig S. Siegel, Woburn; Seng H. Cheng, Wellesley; Simon J. Eastman, Marlboro; John Marshall, Milford, all of Mass.

[73] Assignee: Genzyme Corporation, Cambridge, Mass.

[21] Appl. No.: 352,479

[22] Filed: Dec. 9, 1994

[51] Int. Cl.$^6$ ............... B01F 17/16; C07J 41/00
[52] U.S. Cl. ............... 252/357; 424/450; 514/44; 514/171; 514/182; 514/975; 552/544; 935/52
[58] Field of Search ............... 252/357; 536/22.1, 536/26.1; 514/42, 44, 182, 777, 171, 975; 552/544; 560/6

[56] References Cited

U.S. PATENT DOCUMENTS

| | | | |
|---|---|---|---|
| 2,889,318 | 6/1959 | Bergstrom | 552/544 X |
| 4,394,448 | 7/1983 | Szoka et al. | 435/172 |
| 4,544,545 | 10/1985 | Ryan et al. | |
| 4,569,931 | 2/1986 | Yoshizuka et al. | 514/182 |
| 4,897,355 | 1/1990 | Eppstein et al. | |
| 4,935,413 | 6/1990 | Urano et al. | 514/178 |
| 4,958,013 | 9/1990 | Letsinger | 536/27 |
| 4,971,803 | 11/1990 | Li et al. | 424/450 |
| 5,004,737 | 4/1991 | Kim et al. | 514/182 |
| 5,171,678 | 12/1992 | Behr et al. | 435/172.3 |
| 5,264,618 | 11/1993 | Felgner et al. | 560/244 |
| 5,283,185 | 2/1994 | Epand et al. | |
| 5,334,761 | 8/1994 | Gebeyehu et al. | 564/197 |
| 5,416,203 | 5/1995 | Letsinger | 536/25.34 |
| 5,498,522 | 3/1996 | Porter | 514/674 X |

FOREIGN PATENT DOCUMENTS

| | | |
|---|---|---|
| 0 446 017 A1 | 9/1991 | European Pat. Off. |
| 0 490 379 A3 | 6/1992 | European Pat. Off. |
| 61-7292 | 1/1986 | Japan |
| WO88/00824 | 2/1988 | WIPO |
| WO94/05624 | 3/1994 | WIPO |
| WO94/20520 | 9/1994 | WIPO |
| WO95/02698 | 1/1995 | WIPO |
| WO95/14380 | 6/1995 | WIPO |
| WO95/14381 | 6/1995 | WIPO |
| WO95/14651 | 6/1995 | WIPO |
| WO95/17378 | 6/1995 | WIPO |
| WO95/21812 | 8/1995 | WIPO |
| WO95/24222 | 9/1995 | WIPO |
| WO95/31557 | 11/1995 | WIPO |
| WO96/03977 | 2/1996 | WIPO |
| WO96/10038 | 4/1996 | WIPO |
| WO96/20208 | 7/1996 | WIPO |

OTHER PUBLICATIONS

Leventis et al., "Interactions of Mammalian Cells With Lipid Dispersions Containing Novel Metabolizable Cationic Amphiphiles", *Biochimica et Biophysica Acta*, 1023, 1990, pp. 124–132.

(List continued on next page.)

*Primary Examiner*—Richard D. Lovering
*Attorney, Agent, or Firm*—E. Victor Donahue

[57] ABSTRACT

Novel cationic amphiphiles are provided that facilitate transport of biologically active molecules into cells. Typically, the amphiphiles contain lipophilic groups derived from steroids or from mono or dialkylamines, and two cationic groups, protonatable at physiological pH, derived from amines, alkylamines or polyalkylamines. There are provided also therapeutic compositions prepared typically by contacting a dispersion of one or more cationic amphiphiles, with or without colipids, and therapeutic molecules. Therapeutic molecules that can be delivered into cells according to the practice of the invention include DNA, RNA, polypeptides and low molecular weight organic compounds. Representative uses of the therapeutic compositions of the invention include providing gene therapy, and delivery of antisense polynucleotides or biologically active polypeptides to cells.

7 Claims, 14 Drawing Sheets

OTHER PUBLICATIONS

K. Patel et al., "Modification of Vesicle Surfaces with Amphiphilic Sterols. Effect on Permeability and In Vivo Tissue Distribution", *Biochimica et Biophysica Acta*, 814, 1985, pp. 256–264.

K. Moore et al., "Squalamine: An Aminosterol Antibotic from the Shark", *Proceedings of the National Academy of Sciences USA*, 90, 1993, pp. 1354–1358.

J. Guy–Caffey et al., "Novel Polyaminolipids Enhance the Cellular Uptake of Oligonucleotides", *The Journal of Biological Chemistry*, 270, 1995, pp. 31391–31396.

J. Janne, et al., "Polyamines: From Molecular Biology to Clinical Applications", *Annals of Medicine*, 23, 1991, pp. 241–259.

N. Caplen, et al., "Liposome Mediated CFTR Gene Transfer to the Nasal Epithelium of Patients with Cystic Fibrosis", *Nature Medicine*, 1, 1995, pp. 39–46.

J–S. Remy et al., "Gene Transfer with a Series of Lipophilic DNA Binding Molecules", *Bioconjugate Chemistry*, 5, 1994, pp. 647–654.

J–P. Behr, "Gene Transfer with Synthetic Cationic Amphiphiles: Prospects for Gene Therapy", *Bioconjugate Chemistry*, 5, 1994, pp. 382–389.

J. Felgner, et al., "Enhanced Gene Delivery and Mechanism Studies with a Novel Series of Cationic Lipid Formulations", *The Journal of Biological Chemistry*, 269, 1994, pp. 2550–2561.

F. Barthel et al., "Gene Transfer Optimzation with Lipospermine–Coated DNA", *DNA and Cell Biology*, 12, 1993, pp. 553–560.

J–P. Behr, "Synthetic Gene–Transfer Vectors", *Accounts of Chemical Research*, 26, 1993, pp. 274–278.

P. Hoet, et al., "Kinetics and Cellular Localization of Putrescine Uptake in Human Lung Tissue", *Thorax*, 48, 1993, pp. 1235–1241.

J. Felgner, et al., "Cationic Lipid–Mediated Delivery of Polynucleotides", *Methods (A Companion to Methods in Enzymology)*, 5, 1993, pp. 67–75.

X. Gao, et al., "A Novel Cationic Liposome Reagent for Efficient Transfection of Mammalian Cells", *Biochemical and Biophysical Research Communications*, 179, 1991, pp. 280–285.

J. Rose, et al., "A New Cationic Liposome Reagent Mediating Nearly Quantitative Transfection of Animal Cells", *Biotechniques*, 10, 1991, pp. 520–525.

J. Loeffler, et al., "Lipopolyamine–Mediated Transfection Allows Gene Expression Studies in Primary Neuronal Cells", *Journal of Neurochemistry*, 54, 1990, pp. 1812–1815.

J. Cheetham, et al., "Cholesterol Sulfate Inhibits the Fusion of Sendai Virus to Biological and Model Membranes", *The Journal of Biological Chemistry*, 265, 1990, pp. 12404–12409.

J–P. Behr, et al., "Efficient Gene Transfer into Mammalian Primary Endocrine Cells with Lipopolyamine–Coated DNA", *Proceedings of the National Academy of Sciences, USA*, 86, 1989, pp. 6982–6986.

R. Letsinger, et al., "Cholesteryl–Conjugated Oligonucleotides: Synthesis, Properties, and Activity as Inhibitors of Replication of Human Immunodeficiency Virus in Cell Culture", *Proceedings of the National Academy of Sciences, USA*, 86, 1989, pp. 6553–6556.

L. Stamatos, et al., "Interactions of Cationic Lipid Vesicles with Negatively Charged Phospholipid Vesicles and Biological Membranes", *Biochemistry*, 27, 1988, pp. 3917–3925.

P. Felgner, et al., "Lipofection: A Highly Efficient, Lipid–Mediated DNA–Transfection Procedure", *Proceedings of the National Acadmemy of Sciences, USA*, 84, 1987, pp. 7413–7417.

R. Rando, et al., "The Synthesis and Properties of a Functional Fluorescent Cholesterol Analog", *Biochemica et Biophysica Acta*, 684, 1982, pp. 12–20.

A. Pegg, "Polyamine Metabolism and its Importance in Neoplastic Growth and as a Target for Chemotherapy", *Cancer Research*, 48, 1988, pp. 759–774.

R. Kameji, et al., "Spermidine Uptake by Type II Pulmonary Epithelial Cells in Primary Culture", *American Journal of Physiology*, 256, 1989, pp. C161–C167.

(A) CA: pCMV-CFTR
(42:60)

↑ Forskolin / IBMX    ↓ NPPB (B) CA: pCMV-ß
(42:60)

↑ Forskolin / IBMX    ↓ NPPB $2\mu A/cm^2$ 10 min

The cationic amphiphile ("CA") is spermidine cholesterol carbamate

Ergosterol (double bonds as shown)
Ergosterol B1 (Δ 8, 9; Δ 14, 15; Δ 22, 23)
Ergosterol B1 (Δ 6, 7; Δ 8, 14; Δ 22, 23)
Ergosterol B1 (Δ 7, 8; Δ 14, 15; Δ 22, 23)
Lumisterol (9β-H isomer of ergosterol)

Cholic Acid $r^1$, $r^2$ = OH
Desoxycholic Acid $r^1$ = H, $r^2$ = OH
Chenodesoxycholic Acid $r^1$ = OH, $r^2$ = H
Lithocholic Acid $r^1$, $r^2$ = H Androsterone (A)

(B)

Cholic Acid Derivative r¹, r² = OH
Desoxycholic Acid Derivative r¹ = H, r² = OH
Chenodesoxycholic Acid Derivative r¹ = OH, r² = H
Lithocholic Acid Derivative r¹, r² = H

CATIONIC AMPHIPHILES FOR INTRACELLULAR DELIVERY OF THERAPEUTIC MOLECULES

BACKGROUND OF THE INVENTION

The present invention relates to cationic amphiphilic compounds that are useful for intracellular delivery of biologically active molecules such as nucleic acids. Once introduced to the cytoplasm or nucleus of a cell, many biologically active molecules are capable of influencing cell function. For instance, transfection, the process of introducing expressible DNA and mRNA into cells, can lead to expression and secretion of desirable proteins and polypeptides, and can be used for gene therapy. Similarly, delivery of naturally-occurring and synthetic chemical compounds can be used to modify cell properties and function. However, efficient delivery of these compounds to the cell has often proved difficult if not impossible, since the cell membrane presents a selectively permeable barrier. Accordingly there is a need to develop new methods that facilitate entry of biologically active molecules into cells, and in particular, into cells of patients for therapeutic application.

Reported Developments

In as much as compounds designed to deliver biologically active molecules intracellularly must interact with both non-polar and polar environments (for example, the plasma membrane and cell surface), such compounds are designed typically to contain both polar and non-polar domains. Compounds having both such domains may be termed amphiphiles, and many lipids and synthetic lipids have these properties. Examples of such compounds are found, for example, in the following references.

Felgner, et al., *Proc. Natl. Acad. Sci. USA*, 84, 7413–7417 (1987) disclose use of positively-charged synthetic cationic lipids including N-[1(2,3-dioleyloxy)propyl]-N,N,N-trimethylammonium chloride ("DOTMA"), to form lipid/DNA complexes suitable for transfections. See also Felgner et al., *The Journal of Biological Chemistry*, 269(4), 2550–2561 (1994).

Behr et al., *Proc. Natl. Acad. Sci., USA*, 86, 6982–6986 (1989) disclose numerous amphiphiles including dioctadecylamidologlycylspermine ("DOGS").

U.S. Pat. No. 5,283,185 to Epand et al. describes additional classes and species of amphiphiles including 3β[N-(N¹,N¹-dimethylaminoethane)carbamoyl] cholesterol, termed "DC-chol".

Additional compounds that facilitate transport of biologically active molecules into cells are disclosed in U.S. Pat. No. 5,264,618 to Felgner et al. See also Felgner et al., *The Journal Of Biological Chemistry*, 269(4), pp. 2550–2561 (1994) for disclosure of further compounds including "DMRIE" 1,2-dimyristyloxypropyl-3-dimethylhydroxyethyl ammonium bromide, which is discussed below.

Reference to amphiphiles suitable for intracellular delivery of biologically active molecules is also found in U.S. Pat. No. 5,334,761 to Gebeyehu et al., and Felgner et al., *Methods*(Methods in Enzymology),5, 67–75(1993).

Although the aforementioned classes of molecules have demonstrated activity to facilitate entry of biologically active molecules into cells, at least in vitro, there is a need for compounds having substantially improved performance as, for example, transfectants. Provision of such compounds is particularly important in relation to gene therapy.

SUMMARY OF THE INVENTION

This invention provides for cationic amphiphiles that are particularly effective to facilitating transport of biologically active molecules into cells. Accordingly, there are provided cationic amphiphiles capable of facilitating transport of a biologically active molecules into cells, said amphiphiles having the structure (I),

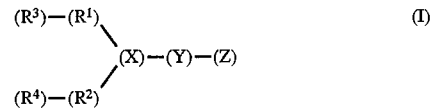

wherein:

Z is a steroid;

X is a carbon atom or a nitrogen atom;

Y is a short linking group, or Y is absent;

$R^3$ is H or alkyl;

$R^1$ is —NH—, an alkylamine, or a polyalkylamine;

$R^4$ is H or alkyl;

$R^2$ is —NH—, an alkylamine, or a polyalkylamine;

and wherein $R^1$ is the same or is different from $R^2$, except that both $R^1$ and $R^2$ cannot be —NH—.

In one preferred embodiment, the steroid component "Z" is selected from the group consisting of 3-sterols, wherein said sterol molecule is linked by the 3—O— group thereof, or by N— in replacement therof, to Y. In a further preferred embodiment, the steroid group is linked to Y (or directly to X) from ring position 17 of the steroid nucleus (see FIGS. 1 and 22), or from the arm that normally extends from position 17 in many steroids (see the structure of cholesterol in FIG. 1) or from any shortened form of said arm.

In other preferred embodiments, within linking group Y are contained no more than about three or four atoms that themselves form a bridge of covalent bonds between X and Z. In a specific preferred embodiment of the invention, Y is a linking group wherein no more than one atom of said group forms a bond with both X and Z, or Y is absent.

Additionally there are provided cationic amphiphiles capable of facilitating transport of biologically active molecules into cells said amphiphiles having the structure (II),

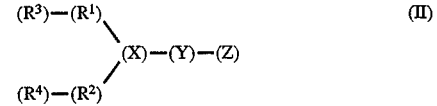

wherein:

Z is an alkylamine or a dialkylamine, linked by the N-atom thereof, to Y, wherein if Z is a dialkylamine, the alkyl groups thereof can be the same or different;

X is a carbon atom or a nitrogen atom;

Y is a short linking group, or Y is absent;

$R^3$ is H or alkyl;

$R^1$ is —NH—, an alkylamine, or a polyalkylamine;

$R^4$ is H or alkyl;

$R^2$ is —NH—, an alkylamine, or a polyalkylamine;

and wherein $R^1$ is the same or is different from $R^2$, except that both $R^1$ and $R^2$ cannot be —NH—.

It is preferred that within linking group Y there are contained no more than about three or four atoms that themselves form a bridge of covalent bonds between X and Z. In a specific preferred embodiment of the invention, Y is a linking group wherein no more than one atom of said group forms a bond with both X and Z, or Y is absent.

The invention provides also for therapeutic compositions that comprise one or more cationic amphiphiles, and one or more biologically active molecules (therapeutic substances), said compositions being formulated typically in a physiologically-acceptable carrier.

In a further aspect, the invention provides a method for facilitating the transfer of a biologically active molecules into cells comprising the steps of: preparing a dispersion of a cationic amphiphile of the invention; contacting said dispersion with a biologicallyactive molecule to form a complex between said amphiphile and said molecule, and contacting cells with said complex thereby facilitating transfer of said biologically-active molecule into the cells.

Optionally, the cationic amphiphile(s) of the invention may be formulated with one or more additional cationic amphiphiles including those known in the art, or neutral colipids such as dioleoylphosphatidylethanolamine, ("DOPE"), to facilitate delivery to cells of the biologically active molecules.

Further additional and representative aspects of the invention are described according to the Detailed Description of the Invention which follows directly.

DETAILED DESCRIPTION OF THE INVENTION

Figure 1:
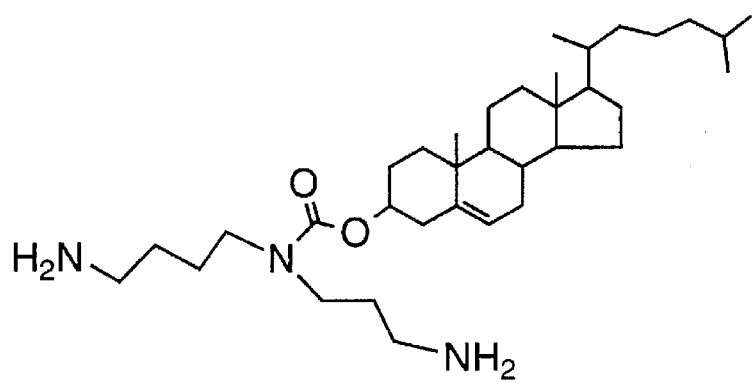
FIG. 1 depicts the molecular structure of spermidine cholesterol carbamate ($N^4$-spermidine cholesteryl carbamate).
Figure 2:
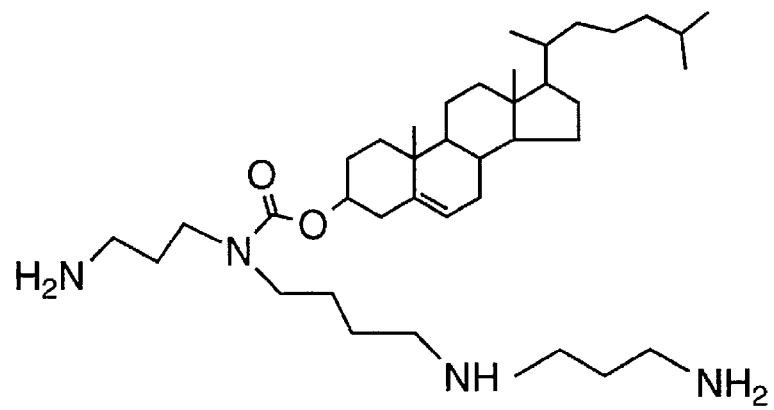
FIG. 2 depicts the molecular structure of spermine cholesterol carbamate. (or $N^4$-spermine cholesteryl carbamate)
Figure 3:
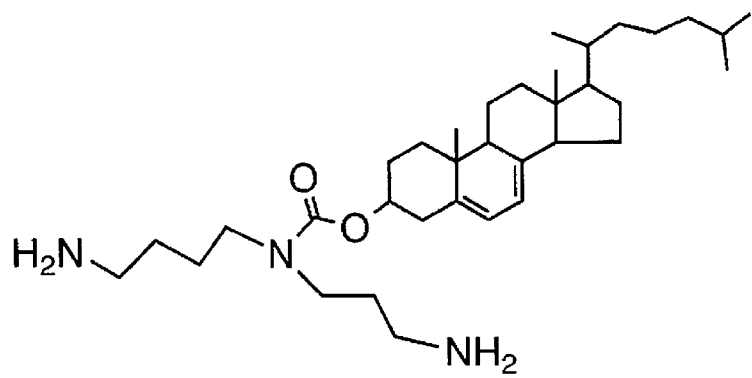
FIG. 3 depicts the molecular structure of spermidine 7-dehydrocholesteryl carbamate (or $N^4$-spermidine 7-dehydrocholesteryl carbamate).
Figure 4:
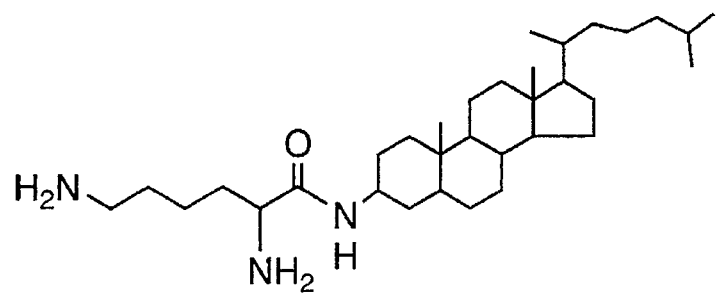
FIG. 4 depicts the molecular structure of lysine 3-N-dihydrocholesteryl carbamate.
Figure 5:
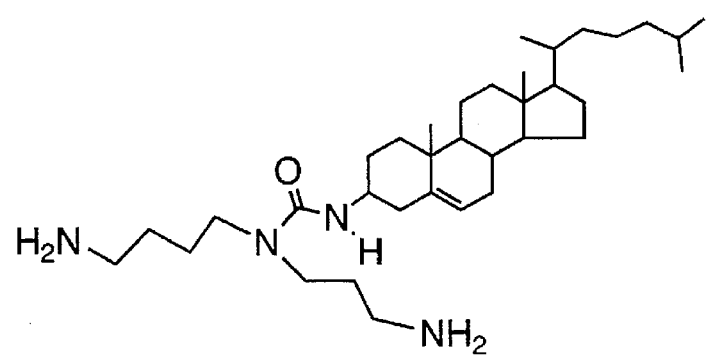
FIG. 5 depicts the molecular structure of spermidine cholestamine urea.

Information Concerning the Structure of Cationic Amphiphiles of the Invention

This invention provides for cationic amphiphile compounds, and compositions containing them, that are useful to facilitate transport of biologically active molecules into cells. The amphiphiles are particularly useful in facilitating the transport of biologically active nucleic acids into cells, and in particular to the cells of patients for the purpose of gene therapy.

Cationic amphiphiles according to the practice of the invention possess several novel features. These features may be seen in comparison with, for example, cationic amphiphile structures such as those disclosed in U.S. Pat. No. 5,283,185 to Epand et al., a representative structure of which is is 3β[N-($N^1,N^1$-dimethylaminoethane)-carbamoyl] cholesterol, commonly known as "DC-chol", and to those disclosed by Behr et al. *Proc. Natl. Acad. Sci., USA*, 86, 6982–6986 (1989), a representative structure of which is dioctadecylamidologlycylspermine ("DOGS").

Cationic amphiphiles of the present invention contain two distinctive structural features: (1) the presence of a lipophilic group (designated "Z" in the depictions of this application) which is connected directly, or through a linking group, to two cationic groups (see below) that themselves comprises one or more amino, alkylamine or polyalkylamine groups, there resulting an overall and novel "T-shaped" structure; and (2) in comparison with numerous art-recognized amphiphiles, the use of a very short linking group to bring into close proximity the lipophilic and cationic regions of the amphiphile. Without being limited as to theory, it is believed that these features contribute substantially to the transfection-enhancing capability of these compounds. As an example, see FIG. 15 which demonstrates that spermidine cholesterol carbamate (a novel amphiphile of the invention) provides enhanced in vivo transfection efficiency in comparision to DC-chol and DMRIE, two well recognized transfectants.

In connection with the practice of the present invention, it is noted that "cationic" means that the R groups, as defined herein, tend to have one or more positive charges at or near physiological pH. Such cationic character may enhance interaction of the amphiphile with therapeutic molecules (such as nucleic acids) or to cell structures (such as plasma membrane glycoproteins) thereby contributing to successful entry into cells. In this regard, the reader is referred to the numerous theories in the art concerning transfection-enhancing function of cationic amphiphiles, none of which is to be taken as limiting on the scope of the amphiphiles of the present invention.

Biological molecules for which transport into cells can be facilitated according to the practice of the invention include, for example, genomic DNA, cDNA, mRNA, antisense RNA or DNA, polypeptides and small molecular weight drugs or hormones.

As aforementioned, characteristic and novel features of the amphiphiles of the invention include first, that the linking group that connects the two cationic amine groups to the lipophilic group is very short, or absent entirely, and second, that the resultant linking of the the two cationic R groups to the lipophilic group forms a T-shaped structure when viewed from the position of atom "X" (a carbon or nitrogen atom) as depicted below, for example, in Structures (I–IV).

In connection with the design of the amphiphiles of the invention the following considerations are of note.

The Linking Group

Preferably the linking group that connects the lipophilic group to the two cationic R group(s) is short. It is preferred that within linking group Y are contained no more than about three or four atoms that themselves form a bridge of covalent bonds between X and Z. Examples of Y groups include —$(CH_2)_2$—, —$(CH_2)$—C=O—, and β-alanine. See structures (I and II) below.

In a specific preferred embodiment of the invention, Y is a linking group wherein no more than one atom of this group forms a bond with both "X" and "Z". Examples of preferred linking groups include —$CH_2$—, >C=S, and >C=O. Alternatively, the linking group "Y" may be absent entirely.

As aforementioned (see Strucutres I and II), "X" forms a connecting point in the amphiphiles to which are also attached the two cationic R groups. As can be seen in FIG. 1, the placement of the nitrogen atom that represents "X" clearly causes the molecule to assume a T-shape.

Lipophilic Groups

Cationic amphiphiles according to the practice of the invention may include therein a variety of structures as lipophilic group, however, two preferred types of structure are (1) steroids and (2) mono or dialkylamines.

(A) Steroids

With respect to the design and orientation of steroids as lipophilic groups according to the practice of the invention, the following considerations are of note. Steroids are widely distributed in the animal, microbial and plant kingdoms. They may be defined as solid alcohols that typically contain, as their basic skeleton, 17 carbon atoms arranged in the form of a perhydrocyclopentenophenanthrene ring system. Accordingly, such compounds include bile acids, cholesterol and related substances, vitamin D, certain insect molting hormones, certain sex hormones, corticoid hormones, certain antibiotics, and derivatives of all of the above wherein additional rings are added or are deleted from the basic structure [see Natural Products Chemistry, K. Nakanashi et al eds., Academic Press, Inc., New York (1974), volume 1, at Chapter 6 for a further discussion of the broad classes of molecules that are understood in the art to be steroids]. Steroids representative of those useful in the practice of the invention are shown in FIGS. 1 to 6, and FIGS. 21 and 22.

Figure 6:
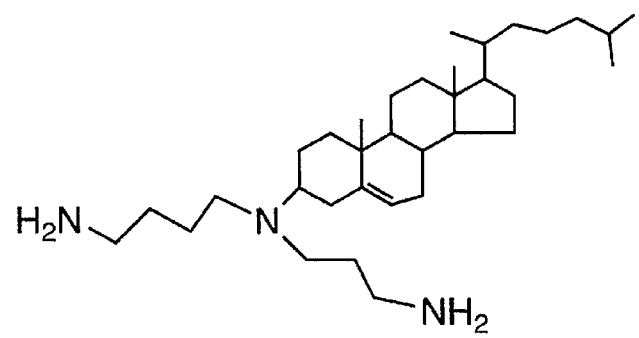
FIG. 6 depicts the molecular structure of N-3-aminopropyl-N-4-aminobutylcholestamine.

As elaborated below, certain preferred amphiphiles of the invention include a steroid component "Z" that is selected from the group consisting of 3-sterols, wherein said sterol molecule is linked by the 3—O— group thereof, or by N— in replacement therof, to Y. See FIGS. 1 and 4. Such structures include, for example, spermidine cholesterol carbamate (See FIG. 1), spermine cholesterol carbamate (see FIG. 2), spermidine 7-dehydrocholesteryl carbamate (FIG. 3), lysine 3-N-dihydrocholesteryl carbamate (FIG. 4), spermidine cholestamine urea (FIG. 5), and N-3-aminopropyl-N-4-aminobutylcholestamine (FIG. 6).

In a further preferred embodiment, the steroid group is linked to Y (or directly to X) from ring position 17 of the steroid nucleus (see FIGS. 1 and 22), or from the arm that normally extends from position 17 in many steroids (see FIGS. 1 and 22) or from any shortened form of said arm.

Figure 21:
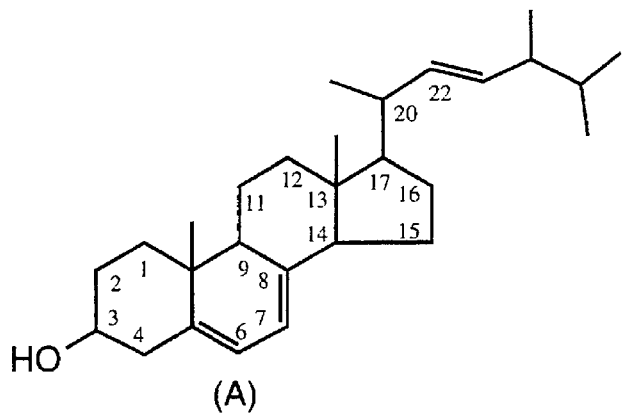
FIG. 21 shows the structure of certain steroids.
Figure 21:
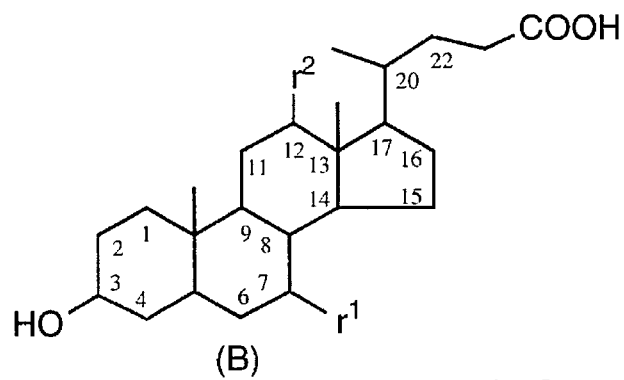
Figure 21:
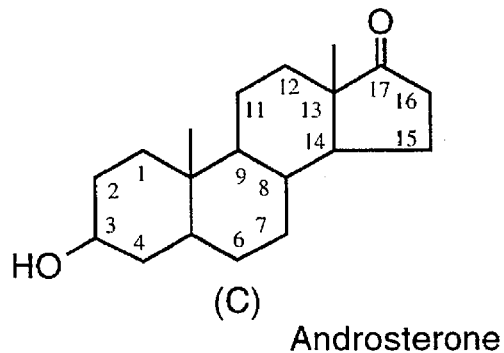
Figure 22:
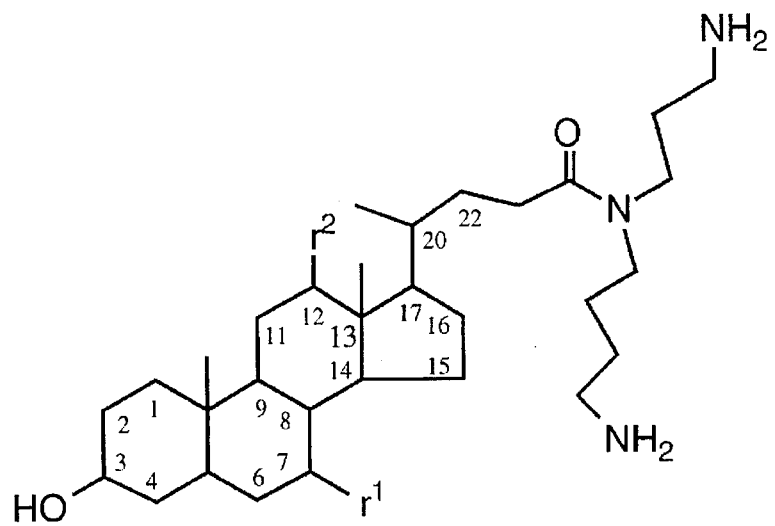
FIG. 22 shows the structure of certain steroids.
Figure 22:
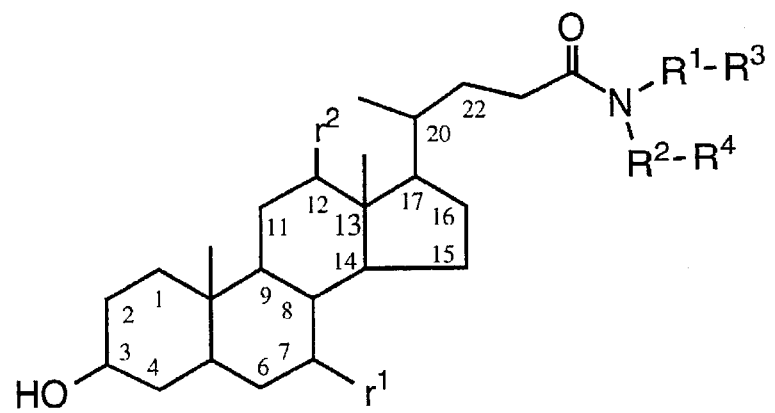

In connection with the selection of steroids for inclusion in the amphiphiles of the invention, it is preferred that the molecules have structures which can be metabolized by the body and are nontoxic at the doses thereof that are used. Preferred are steroids such as cholesterol and ergosterol that are substantially non toxic and which possess biologically normal stereospecificity in order to facilitate their safe metabolism in patients. Additional steroids useful in the practice of the invention include, for example, ergosterol B1, ergosterol B2, ergosterol B3, androsterone, cholic acid, desoxycholic acid, chenodesoxycholic acid, lithocholic acid and, for example, various derivatives thereof as are shown in the panels of FIGS. 21 and 22.

With respect to the orientation of the steroid lipophilic group, that is, how the group is attached (with or without a linker) to the cationic amine groups of an amphiphile, the following further information is of note. Any ring position or substituent on the steroid can in general be used as point of attachment. It is preferred, however, to use a point of attachment that (1) mimimizes the complexity of chemical syntheses, and (2) is positioned near either "end" of the steroid molecule, for example, a position near ring position 3, or near ring position 17 (or the arm that typically extends therefrom). Such positions provide an orientation of the steroid with respect to the rest of the amphiphile structure that faciliates bilayer formation, micelle formation, and/or stabilizes interaction with the biologically active molecules to be carried into the target cells. One such structure therefore is shown in FIG. 22 (panel A). With respect to this type of structure, it is further preferred that any polar groups, such as may be attached to ring position 3, be either removed or capped (for example, hydroxy as methoxy) to avoid potentially destabilizing bilayer or micelle structures. The representation in FIG. 22 of cationic amphiphiles in which the steroid lipophilic group thereof is linked to the cationic amine groups thereof through steroid ring position 17 is but an example of the invention. Similarly, the representation in FIGS. 1 to 4 of cationic amphiphiles in which the steroid lipophilic group thereof is linked to the cationic amine groups thereof through steroid ring position 3 is an example of the invention. As aforementioned, use of any steroid ring position (or moiety or branch extending therefrom) as point of attachment is within the practice of the invention.

(B) Lipophilic Alkylamine Groups

According to the practice of the invention, Z is also represented by an alkylamine or a dialkylamine, linked by the N-atom thereof, to Y, wherein if Z is a dialkylamine, the alkyl groups thereof can be the same or different.

Figure 7:
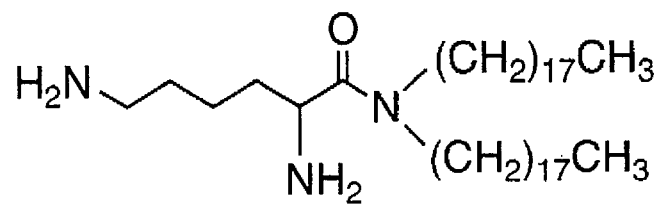
FIG. 7 depicts the molecular structure of N,N-dioctadecyllysineamide.
Figure 8:
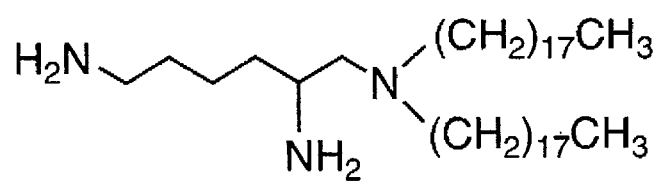
FIG. 8 depicts the molecular structure of $N^1,N^1$-dioctadecyl-1,2,6-triaminohexane.
Figure 9:
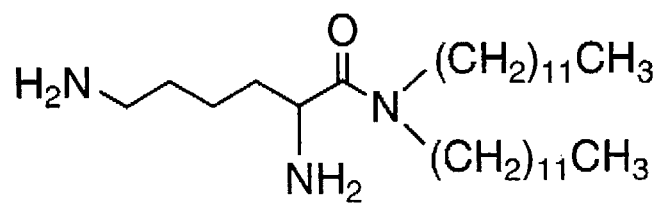
FIG. 9 depicts the molecular structure of N,N-didodecyllysineamide.
Figure 10:
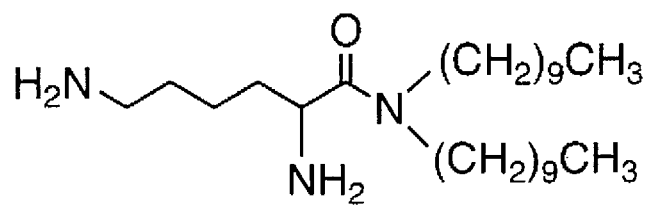
FIG. 10 depicts the molecular structure of N,N-didecyllysineamide.
Figure 11:
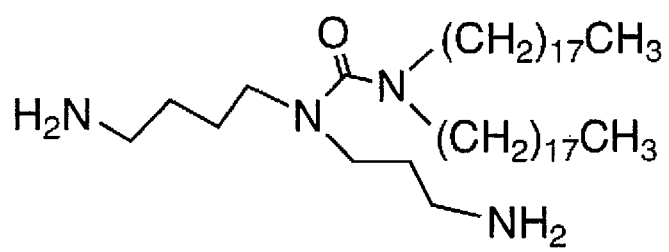
FIG. 11 depicts the molecular structure of spermidine-N,N-dioctadecyl urea.
Figure 12:
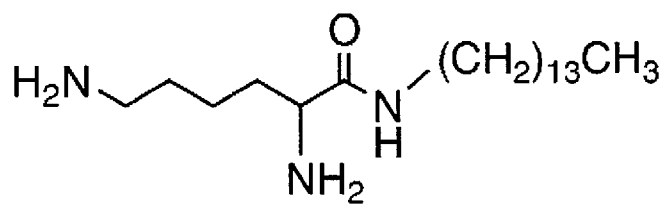
FIG. 12 depicts the molecular structure of N-myristyllysineamide.

Representative cationic amphiphiles according to the practice of the invention that contain an alkyl amine or dialkylamine as lipophilic group include, for example, N,N-dioctadecyllysineamide (FIG. 7), $N^1,N^1$-dioctadecyl-1,2,6-triaminohexane (FIG. 8), N,N-didodecyllysineamide (FIG. 9), N,N-didecyllysineamide (FIG. 10), spermidine-N,N-dioctadecyl urea (FIG. 11), and N-myristyllysineamide (FIG. 12).

In connection with the selection of suitable alkylamine or dialkylamine groups for inclusion at position Z in the amphiphiles of the invention, the group should not be so large in molecular weight that it interferes with the solubility or micelle forming properties of the amphiphile. Selection of Groups $R^1$, $R^2$, $R^3$, and $R^4$ According to the practice of the invention $R^3$ and $R^4$ are H or alkyl. $R^1$ and $R^2$ represent structures recognized in the art as being simple "alkylamines" or extended versions thereof, termed here "polyalkylamines". Both $R^1$ and $R^2$ can be —NH—, an alkylamine, or a polyalkylamine, and can be the same or different from each other, except that both $R^1$ and $R^2$ cannot be —NH— in order to (1) preserve the "T-shape" of the resultant compound, and (2) to provide for the stability thereof.

Representative alkylamine structures are defined as follows:

(a) —NH—(CH$_2$)$_n$— where n is a whole number;

(b) —[NH—(CH$_2$)$_{(x)}$]$_n$— where x and n are whole numbers; and (c) —[NH—(CH$_2$)$_{(x)}$]$_n$—[NH—(CH$_2$)$_{(y)}$]$_m$—[NH—(CH$_2$)$_{(z)}$]$_p$— where x, y, z, m, n, and p are whole numbers, but none of x, y, and z are 0 or 1.

In connection with interpreting the structural diagrams herein, it is intended that the attachment of structures (a), (b), and (c) above to atom "X" is through the right hand side of structures (a), (b), and (c) as shown above, that is through a CH$_2$ moiety. Additionally, for the purposes of the invention, "whole number" means 0 and the natural numbers 1,2,3,4,5,6 . . . and up.

With respect to the design of such structures for inclusion in cationic amphiphiles, the following considerations are of note. Any combination of alternating amine and alkyl moieties creates an R structure within the scope of the invention. A polyalkylamine may be represented, for example, by formula (c) above, although many more structures (such structures being within the scope of the invention) can be depicted by extending the number of, or types or combinations of, aklylamine subuinits within the structure. Certain combinations of such structures are, of course, difficult to make, or are unstable. For example, it is recognized that the R sequence —NH—CH$_2$—NH—CH$_2$— would be unstable. Accordingly, its use in the practice of the invention is not preferred. Additionally, a polyalkylamine group that is very long may interfere with the solubility of the amphiphile, or its ability to stably interact with the biologically active molecule selected for intracellular delivery. In this regard, polyalkylamines having a backbone length of about 40 nitrogen and carbon atoms, or more, may not be suitable for inclusion in amphiphiles. However, for each such proposed structure, its properties may be determined by experimentation, and its use is nonetheless within the practice of the invention.

General Features of the Amphiphiles of the Invention

Structures (I) and (II) below are representative of structures that can be used to depict the aforementioned novel features.

Cationic amphiphiles are provided according to structure (I),

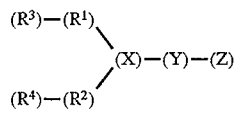

wherein:

Z is a steroid linked to Y;

X is a carbon atom or a nitrogen atom;

Y is a short linking group, or Y is absent;

R$^3$ is H or alkyl;

R$^1$ is —NH—, an alkylamine, or a polyalkylamine;

R$^4$ is H or alkyl;

R$^2$ is —NH—, an alkylamine, or a polyalkylamine;

and wherein R$^1$ is the same or is different from R$^2$, except that both R$^1$ and R$^2$ cannot be —NH—.

Cationic amphiphiles are also provided according to structure (II),

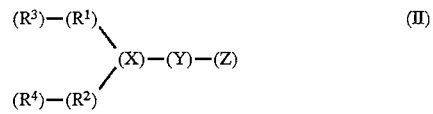

wherein:

Z is an alkylamine or a dialkylamine, linked by the N-atom thereof, to Y, wherein if Z is a dialkylamine, the alkyl groups thereof can be the same or different;

X is a carbon atom or a nitrogen atom;

Y is a short linking group, or Y is absent;

R$^3$ is H or alkyl;

R$^1$ is —NH—, an alkylamine, or a polyalkylamine;

R$^4$ is H or alkyl;

R$^2$ is —NH—, an alkylamine, or a polyalkylamine;

and wherein R$^1$ is the same or is different from R$^2$, except that both R$^1$ and R$^2$ cannot be —NH—.

In connection with providing cationic amphiphiles according to structures (I) and (II), the following information is provided. Cationic amphiphile species may be combined according to the practice of the invention so that two or more species thereof are used to facilitate entry of a biologically active molecule into a target cell. It is known in the art that certain species of amphiphile may facilitate crossing the plasma membrane of a target cell, whereas certain amphiphiles may be more useful for facilitating movement of the biologically active molecule into or out of intracellular compartments. Thus combinations of amphiphiles(with or without one or more colipids), are also useful as transfecting compositions. Additionally, such compositions may be blended depending on whether the target cells are in vivo or in vitro.

Preferred cationic amphiphiles provided according to the practice of the invention are represented by structure (III),

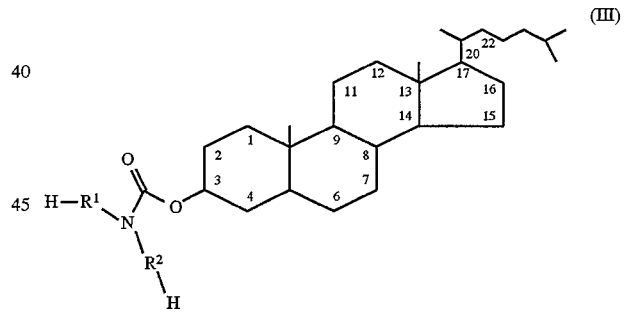

wherein:

Z is a steroid linked by the 3—O— group thereof to Y, it being additionally understood that a double bond at ring position 5–6 is an optional component thereof;

X is a nitrogen atom;

Y is a carbonyl group;

R$^1$ is —[NH—(CH$_2$)$_{(x)}$]$_n$—[NH—(CH$_2$)$_{(y)}$]$_m$—, wherein x, y, m, and n are intergers, the sum of n and m is 1 or 2, neither x nor y is 1, and neither x nor y is zero unless the corresponding n or m is zero;

R$^2$ is —[NH—(CH$_2$)$_{(x)}$]$_n$—[NH—(CH$_2$)$_{(y)}$]$_m$—, wherein x, y, m, and n are intergers, the sum of n and m is 1 or 2, neither x nor y is 1, and neither x nor y is zero unless the corresponding n or m is zero, and wherein R$^1$ is the same or is different from R$^2$.

Further such amphiphiles are represented by structure (IV):

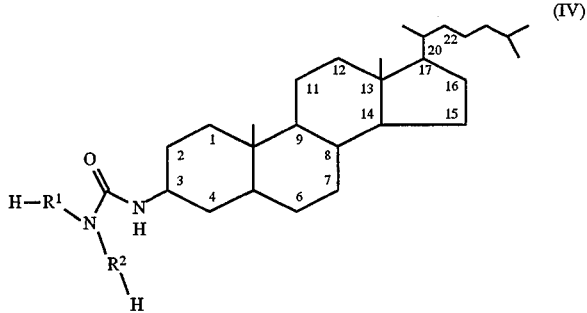

(IV)

wherein:

Z is a steroid linked by the 3—N— group thereof to Y it being additionally understood that a double bond at ring position 5–6 is an optional component thereof;

X is a nitrogen atom;

Y is a carbonyl group;

$R^1$ is —[NH—(CH$_2$)$_{(x)}$]$_n$—[NH—(CH$_2$)$_{(y)}$]$_m$—, wherein x, y, m, and n are intergers, the sum of n and m is 1 or 2, neither x nor y is 1, and neither x nor y is zero unless the corresponding n or m is zero;

$R^2$ is —[NH—(CH$_2$)$_{(x)}$]$_n$—[NH—(CH$_2$)$_{(y)}$]$_m$—, wherein x, y, m, and n are intergers, the sum of n and m is 1 or 2, neither x nor y is 1, and neither x nor y is zero unless the corresponding n or m is zero, and wherein $R^1$ is the same or is different from $R^2$.

Preparation of Therapeutic Compositions and Administration Thereof

The cationic amphiphilic compounds of the invention provide a method of introducing biologically-active molecules into cells of tissues in patients. Additionally, biologically active molecules may be introduced into cells in vitro such as in tissue culture, or ex vivo. Such introduction has, accordingly, therapeutic use and also diagnostic use. Additionally the cationic amphiphiles of the invention can similarly be used to introduce biologically active molecules into plant cells, such as plant embryos in tissue culture.

As aforementioned, the biologically-active molecule can be a nucleic acid, including genomic DNA, cDNA, mRNA, or an antisense nucleic acid. The biologically active molecule may also be a protein, polypeptide, or a synthetic or naturally-occurring low molecular weight compound.

Dosages of pharmaceutical preparations containing the amphiphiles (and the biologically active molecules complexed therewith) of the invention will vary, depending on factors such as half-life of the biologically-active molecule, potency, the route of administration, and the condition of the patient. Such factors are capable of determination by those skilled in the art. Nebulizing devices, powder inhalers, and aerosolized solutions are representative of methods that may be used to administer such preparations. These methods of administration may be used to provide small, highly-accurate dosages of these preparations and are particularly effective for delivery to the respiratory tract.

In still other embodiments, amphiphile-containing preparations of the invention can be administered via one of the traditional modes (e.g., orally, parenterally, transmucosally) or by injection of a preparation into a body cavity of the patient, or by using a sustained-release formulation containing a biodegradable material, or by onsite delivery using additional micelles, gels and liposomes.

In connection with complexing DNA with the cationic amphiphiles of the invention to provide a therapeutic composition, and to then deliver said composition to a patient (or to cells in vitro), it has been determined that the cationic amine portion of the amphiphile may be (but need not be) protonated, in whole or part, at any timepoint in the procedure that is prior to contact of the preparation with a buffered body fluid.

Additionally, the DNA/amphiphile compositions of the invention may also be formulated with excipients (such as the sugars lactose, trehalose, sucrose, or mannitol) and may also be lyophilized in the presence thereof prior to use. It is possible, however, that high excipient concentrations may interfere with successful transfection of the biologically active molecule upon contact with the tissue of a patient. Additionally, formulations in which the DNA/amphiphile combination is prepared (or stored) solely in deionized water may cause osmotic harm to tissues upon contact therewith, particularly the damaged lung tissue of a cystic fibrosis patient. Accordingly, the presence of a modest quantity of an osmotically active substance therein, such as 50 mM of NaCl, may be preferred.

Methods of Syntheses

The following methods illustrate production of certain of the cationic amphiphiles of the invention. Those skilled in the art will recognize other methods to produce these compounds, and to produce also the other compounds of the invention.

Spermidine Cholesterol Carbamate

Figure 13:
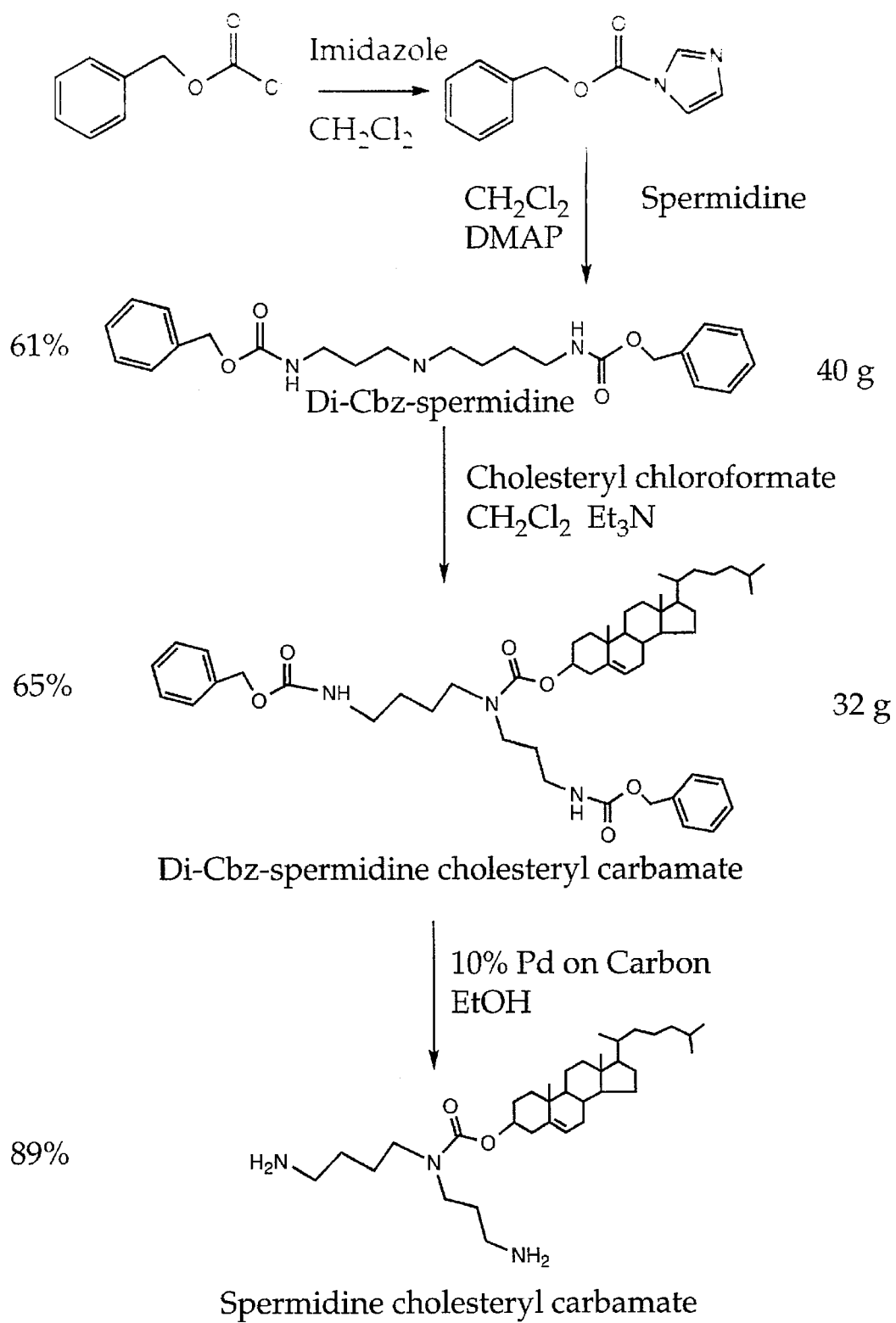
FIG. 13 provides a route of synthesis for spermidine cholesterol carbamate.

Spermidine cholesterol carbamate (FIG. 1) was synthesized according to the following procedure which is outlined in FIG. 13.

Synthesis of $N^1,N^8$-DiCBZ-$N^4$—Spermidine Cholesterol Carbamate $N^1,N^8$-dicarbobenzoxyspermidine (61% yield, m.p. 104°–105° C.) was prepared according to the procedure of S. K. Sharma, M. J. Miller, and S. M. Payne, J. Med. Chem., 1989, 32, 357–367. The $N^1,N^8$-dicarbobenzoxyspermidine (25 g, 60.5 mmol) and triethylamine (25 ml, 178 mmol) were dissolved in 625 ml of anhydrous methylene chloride, cooled to 0°–4° C. and stirred under $N_2$. Cholesteryl chloroformate (27.2 g, 60.6 mmol) was dissolved in 250 ml of methylene chloride and added to the reaction over a 20 minute period. A white precipitate formed upon addition. After the addition was complete, the reaction was stirred at 0°–4° C. for 10 minutes and then at room temperature for 1.5 hr. At this point, the white precipitate completely dissolved. The reaction was followed by TLC with hexane/ethyl acetate 6/4 as eluent (product Rf=0.25). To this reaction mixture was added 625 ml of methylene chloride and 625 ml of water. The layers were then allowed to separate. The organic layer was dried over $MgSO_4$ and filtered. The filtrate was concentrated in vacuo to give an oil. Vacuum drying was then carried out overnight. This crude product had a glue-like consistency. The crude product was purified by column chromatography (2 kg silica gel, eluent-hexane/ethyl acetate 6/4) to give 46.8 g of the 3-β-[$N^4$-($N^1,N^8$-dicarbobenzoxyspermidine)carbamoyl] cholesterol (also described herein as $N^1,N^8$-diCBZ-$N^4$-spermidine cholesterol carbamate) in 93% yield.

Final Synthesis of Spermidine Cholesterol Carbamate

To 6.0 grams of 10% palladium on activated carbon under $N_2$ was added a solution of 30 grams of 3-β-[$N^4$-($N^1,N^8$-dicarbobenzoxyspermidine)carbamoyl] cholesterol in 1 liter of ethanol, see FIG. 13. The reaction mixture was purged with $N_2$ and stirred under $H_2$ (atmospheric pressure) for 18 hr. The mixture was again purged with $N_2$ and filtered through a 10 g bed of celite. The filter cake was washed with 2 liters of 10% triethylamine in ethanol and the combined filtrates were concentrated in vacuo to a gel. The product was then dried under vacuum overnight to a sticky solid. This crude product was purified by column chromatography (2 kg of silica gel, eluent - 4 L of chloroform/methanol 95/5 followed by 30 L of chloroform/methanol/iso-propylamine 95/5/5, Rf=0.24) to obtain 13.1 g of the desired spermidine cholesterol carbamate in 64% yield. HPLC (C-18 reversed phase column, linear gradient elution profile - methanol/iso-propanol/water/trifluoroacetic acid 60/20/20/0.1 to methanol/iso-propanol/trifluoroacetic acid 70/30/0.1 to methanol/iso-propanol/chloroform/trifluoroacetic acid 60/20/20/0.1) analysis of this material showed it to be 99.2% pure with the 7-dehydrocholesterol analog present at a level of 0.8%.

In connection with this example and those that follow, it is noted that all TLC plates were visualized with phosphomolybdic acid.

Spermine Cholesterol Carbamate

Figure 14:
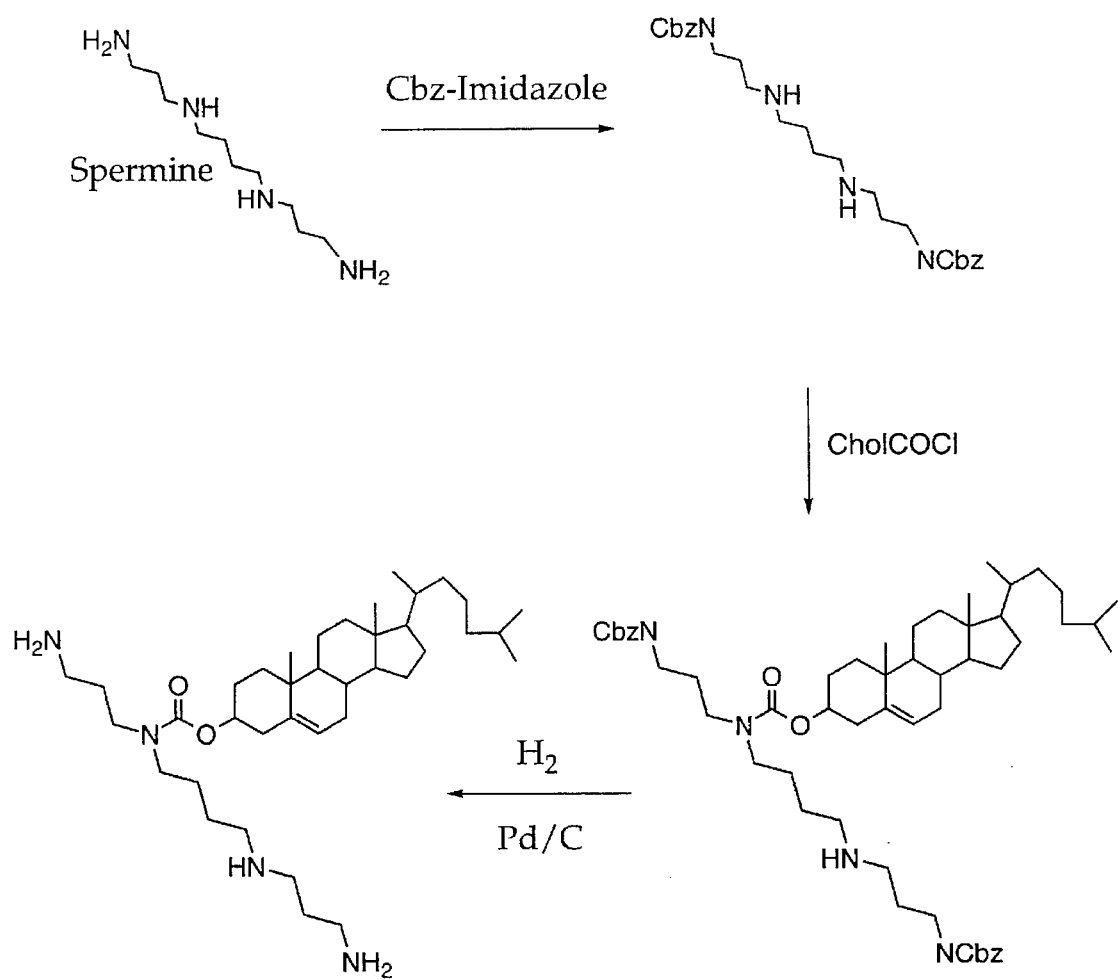
FIG. 14 provides a route of synthesis for spermine cholesterol carbamate.

Spermine cholesterol carbamate (FIG. 2) was prepared according to the following procedure which is outlined in FIG. 14. $N^1,N^{12}$-diCBZ-spermine Benzylchloroformate (1.76 g, 1.5 ml, 10.36 mmol) was dissolved in methylene chloride (5 ml) and placed in a three neck flask under a nitrogen atmosphere. Imidazole (1.4 g, 20.6 mmol) was dissolved in methylene chloride (20 ml) and placed in an addition funnel. The three neck flask was cooled to 0° C. and the imidazole solution was added gradually over 20 min. The mixture was stirred at room temperature for 1 hour and then methylene chloride ( 25 mL) and citric acid (10%, 25 ml) were added. The layers were separated and the organic fraction was washed with citric acid (10%, 25 ml). The organic component was dried over magnesium sulfate and concentrated in vacuo. The residue was dried under high vacuum for 1 hour at ambient temperature.

To the residue was added dimethylaminopyridine (35 mg), methylene chloride (25 ml) and the mixture was cooled to 0° C., under a nitrogen atmosphere. To an addition funnel was added a solution of spermine (1 g, 4.94 mmol) in methylene chloride (25 ml). The spermine solution was added gradually over 15 min. The reaction mixture was stirred overnight at ambient temperature and then concentrated in vacuo. The residue was dissolved in ethyl acetate (80 ml) and washed three times with water (15 ml). The organics were dried over magnesium sulfate, filtered and concentrated in vacuo to give a crude white solid. The material was purified by flash chromatography (65 g silica gel, 100:100:10 $CHCl_3:MeOH:NH_4OH$, product Rf.=0.33), to give after drying under high vacuum 1.01 g (2.146 mmol, 43% yield) of product.

$N^1,N^{12}$-diCBZ-$N^4$-Spermine Cholestryl Carbamate

Cholesteryl chloroformate (964 mg, 2.15 mmol) was dissolved in chloroform (10 ml) and added dropwise to a cooled (0° C.) solution of $N^1,N^{12}$-diCBZ spermine (1.01 g, 2.15 mmol), triethylamine (1 ml) in chloroform (10 ml). The reaction was allowed to warm to room temperature and stirred for 2 hours. To the reaction solution was added water (25 ml) and chloroform (25 ml). The layers were separated and the organic fraction dried over magnesium sulfate. The solution was concentrated in vacuo to give a crude material that was purified by flash chromatography (68 g silica gel, $MeOH/CHCl_3$ ¼, product Rf.=0.36) to give 1.23 g (1.39 mmol, 65% yield) of product.

$N^4$-Spermine Cholesteryl Carbamate $N^1,N^{12}$-diCBZ-$N^4$-spermine cholesteryl carbamate (262 mg, 0.300 mmol) was dissolved in 5 ml of acetic acid anal 45 mg of 10% Pd on C was added. The solution was purged with nitrogen and stirred under hydrogen at atmospheric pressure. The hydrogenolysis was allowed to proceed for 7 hours. The reaction mixture was filtered and the catalyst was washed with 40 ml of ethyl acetate/acetic acid 9/1 and the filtrate will be concentrated in vacuo to give a residue. The crude product was dissolved in 35 mL of 1N NaOH and extracted three times with 40 ml of chloroform/methanol 9/1. The combined organic fractions were washed with 20 mL of water and dried over $Na_2SO_4$. The solution was filtered, concentrated in vacuo and dried under vacuum to give 125 mg of the desired product in 67% yield.

In connection with the above procedure, it is noted that the hydrogenolysis should be carried out under acidic conditions, in order to minimize the poisoning of the catalyst.

Urea analogs—such as spermine or spermidine cholestamine urea—can be prepared by a sequence of reactions well known to those versed in the art of organic synthesis. For example an amine can be treated with an equal molar amount of carbonyldiimidazole followed by the addition of a second amine to give the desired urea.

N,N-Dioctadecyllysineamide

N,N-dioctadecyllysineamide (FIG. 7) was prepared according to the following procedure. N,N-dioctadecylamine (1.35 g, 2.58 mmol, Fluka) and L-Nα,Nε-diBOClysine N-hydroxysuccinimide ester (1.00 g, 2.58 mmol, Sigma) were combined in 15 ml of methylene chloride and 2 ml triethylamine was added. The reaction mixture was heated briefly to effect complete dissolution and then stirred at ambient temperature overnight. Water (20 ml) and methylene chloride (50 ml) were added to the reaction mixture and the layers were separated. The aqueous fraction was extracted a second time with 50 ml methylene chloride. The combined organic fractions were dried over $MgSO_4$, filtered and concentrated in vacuo. The residue was purified by column chromatography (150 g silica gel, eluent - hexane/ethyl acetate 8/2). The purified material, N,N-dioctadecyl-Nα,Nε-diBOClysineamide (1.59 g) was dissolved in 25 ml of chloroform and stirred for 2 hr. while HCl gas was bubbled through the solution. This solution was purged with $N_2$ gas and concentrated in vacuo. N,N-dioctadecyllysineamide (1.34 g) was obtained in 68% yield as the di HCl salt.

Lysine 3-N-Dihydrocholesteryl Carbamate

Lysine 3-N-dihydrocholesteryl carbamate (FIG. 4) was prepared according to the following procedure.

To a solution of dihydrocholesterol (5.0 g, 12.9 mmol, Aldrich), phthalimide (2.0 g, 13.6 mmol, Aldrich), and triphenylphosphine (3.8 g, 13.6 mmol, Aldrich) in THF (20 ml, Aldrich) stirred at 0° C. under a nitrogen atmosphere was added dropwise diethylazodicarboxylate (2.3 ml, 14.5 mmol, Aldrich). Upon the completion of addition the reaction mixture was allowed to warm to ambient temperature and stirred overnight. The reaction mixture was concentrated in vacuo to a residue. This residue was dissolved in 50 ml hexane/ethyl acetate 95/5 and a precipitate formed. The mixture was filtered. The filtrate was concentrated to dryness in vacuo, dissolved in 25 ml of hexane/ethyl acetate 95/5 and chromatographed on 200 g silica gel (eluent 2 L hexane/ethyl acetate 95/5 then 1 L hexane/ethyl acetate 90/10). A 76% yield of the desired 3-phthalimidocholestane (5.43 g) was obtained.

The 3-phthalimidocholestane (5.40 g, 9.75 mmol) was dissolved in 60 mL of methanol and anhydrous hydrazine (3.1 ml, 99 mmol) was added. The reaction mixture was stirred and heated at reflux under a nitrogen atmosphere for 4 hr. This mixture was then cooled to room temperature, 3.1 mL of concentrated HCl was added and the resulting mixture was heated at reflux overnight. Upon cooling to ambient temperature, 100 ml of diethyl ether and 50 ml of 1N NaOH were added (final pH of 10.1) and the layers were separated. The aqueous layer was extracted with 50 ml of diethyl ether and the combined organic fractions were filtered. The filtrate was concentrated in vacuo and the residue was purified by silica gel chromatography (chloroform/methanol 90/10) to give 2.24 g of 3-aminocholestane in 59% yield.

L-Nα,Nε-diBOClysine N-hydroxysuccinimide ester (286 mg, 0.644 mmol, Sigma) and 3-aminocholestane (250 mg, 0.644 mmol) were dissolved in 5 mL of methylene chloride, 0.1 mL of triethylamine was added and the resulting solution was stirred under a nitrogen atmosphere at ambient temperature overnight. To the reaction mixture was added 10 mL of water and 25 mL of methylene chloride and the layers were separated. The aqueous layer was extracted with 25 mL of methylene chloride and the combined organic fractions were dried over $MgSO_4$ and filtered. The filtrate was concentrated in vacuo and the residue was purified by chromatography on 25 g of silica gel (eluent - hexane/ethyl acetate 6/4, sample applied in hexane/ethyl acetate 9/1). The purified material was dissolved in 25 mL of chloroform and HCl gas was bubbled through the solution for 2 hr. followed by nitrogen for 10 min. The solution was concentrated in vacuo to give 299 mg of the desired product in 79% yield as the dihydrochloride salt.

$N^1,N^1$-Dioctadecyl-1,2,6-Triaminohexane $N^1,N^1$-Dioctadecyl-1,2,6-triaminohexane (FIG. 8) was prepared as follows. To N,N-Dioctadecyl-Nα,Nε-diBOClysineamide (760 mg, 0.823 mmol) in 30 ml anhydrous THF stirred at ambient temperature was added $LiAlH_4$ (185 mg, 4.87 mmol) in portions. The reaction mixture was stirred at ambient temperature overnight under a nitrogen atmosphere. The reaction was quenched by the dropwise addition of 2 ml water and the resulting solution was concentrated in vacuo. To this residue was added in order 10 mL of 1M HCl, 50 ml of methylene chloride, and 10 ml of 1M NaOH (final pH=10). The layers were separated and the aqueous fraction was extracted a second time with 50 ml of methylene chloride. The combined organic layers were dried over $MgSO_4$ and filtered. The filter cake was washed with 50 ml of methylene chloride. The combined filtrates were concentrated in vacuo to give 700 mg of crude product. The crude product was purified by column chromatography (80 g silica gel, eluent - hexane/ethyl acetate 7/3). The fractions containing the purified product were combined and concentrated in vacuo to obtain 490 mg of the product protected as the diBOC derivative. To 200 mg of this diBOC derivative was added 4 ml of chloroform and 1 ml of TFA. The resulting reaction mixture was stirred at ambient temperature for 2 hr and concentrated in vacuo. The residue was dissolved in 25 ml of water and 25 mL of methylene chloride and adjusted to pH 10 with approximately 2 ml of concentrated ammonium hydroxide. The layers were separated and the aqueous layer was extracted a second time with 25 ml of methylene chloride. The organic fractions were combined, dried over $Na_2SO_4$ and concentrated in vacuo. The resulting residue was dissolved in 10 ml of diethyl ether. HCl gas was bubbled through the solution for 2 minutes and the solution was cooled at 4° C. overnight. The precipitated product was collected by filtration, washed with cold (4° C. diethyl ether, and dried under vacuum to obtain 160 mg of the desired product in 67% yield.

Co-Lipids

Representative colipids that are useful according to the practice of the invention for mixing with one or more cationic amphiphiles include dioleoylphosphatidylethanolamine, diphytanoylphosphatidylethanolamine, lyso-phosphatidylethanolamines other phosphatidylethanolamines, phosphatidylcholines, lyso-phosphatidylcholines and cholesterol. Typically, a preferred molar ratio of cationic amphiphile to colipid is 1:1. However, it is within the practice of the invention to vary this ratio (see Example 3 below), including also over a considerable range.

EXAMPLES

The following Examples are representative of the practice of the invention.

Example 1—Cell Transfection Assay

Separate 3.35 μmole samples of spermidine cholesterol carbamate and the neutral lipid dioleoylphosphatidylethanolamine ("DOPE") were each dissolved in chloroform as stock preparations. Following combination of the solutions, a thin film was produced by removing chloroform from the mixture by evaporation under reduced pressure (20 mm Hg). The film was further dried under vacuum (1 mm Hg) for 24 hours. To produce a dispersed suspension, the lipid film was then hydrated with sterile deionized water (1 ml) for 10 minutes, and then vortexed for 1 minute (sonication for 10 to 20 seconds in a bath sonicator may also be used, and sonication has proved useful for other amphiphiles such as DC-chol). The resulting suspension was then diluted with 4 ml of water to yield a solution that is 670 μM in cationic amphiphile and 670 μM in neutral colipid.

For preparation of the transfecting solution, DNA encoding for β-galactosidase (pCMVβ, ClonTech., Palo Alto, Calif.) was dissolved in OptiMEM culture medium (Gibco/BRL No. 31885-013). The resulting solution had a DNA concentration of 960 μM (assuming an average molecular weight of 330 daltons for nucleotides in the encoding DNA).

The following procedure was used to test a 1:1 molar mixture of the cationic amphiphile spermidine cholesterol carbamate in combination with DOPE. A 165 μl aliquot of spermidine cholesterol carbamate (670 μM) containing also the colipid (at 670 μM) was pipetted into 8 separate wells in a 96-well plate containing OptiMEM (165 μl) in each well. The resulting 335 μM solutions were then serially diluted 7 times to generate 8 separate amphiphile-containing solutions having concentrations ranging from 335 μM to 2.63 μM, with each resultant solution having a volume of 165 μl. Thus, 64 solutions were prepared in all, there being 8 wells each of 8 different concentrations of amphiphile/DOPE.

Independently, DNA solutions (165 μl, 960 μM) were pipetted into 8 wells containing OptiMEM (165 μl), and the resulting 480 μM solutions were then serially diluted 7 times to generate 8 separate 165 μl solutions from each well, with the concentrations of DNA in the wells ranging from 480 μM to 3.75 μM.

The 64 test solutions (cationic amphiphile: neutral lipid) were then combined with the 64 DNA solutions to give separate mixtures in 64 wells, each having a volume of 330 μl, with DNA concentrations ranging from 240 μM to 1.875 μM along one axis, and lipid concentrations ranging from 167 μM to 1.32 μM along the other axis. Thus 64 solutions were prepared in all, each having a different amphiphile: DNA ratio and/or concentration. The solutions of DNA and amphiphile were allowed to stand for 15 to 30 minutes in order to allow complex formation.

A CFT-1 cell line (human cystic fibrosis bronchial epithelial cells immortalized with papillomavirus) provided by Dr. James Yankaskas, University of North Carolina, Chapel Hill, was used for the in vitro assay. The cells were cultured in Hams F12 nutrient media (Gibco/BRL No. 31765-027) supplemented with 2% fetal bovine serum ("FBS", Irvine Scientific, No. 3000) and 7 additional supplements. Cells were then plated into 96-well tissue culture plates at a density of approximately 7,500 cells/well. Before being used in the assay, cells were allowed to grow for periods of 5–7 days until a confluent pattern had been achieved.

Following the allotted time period, three 96-well plates with CFT-1 cells were aspirated in order to remove the growth medium. The various concentrations of DNA-lipid complex (in 100 μl aliquots) were transferred to each of three 96-well plates bringing the DNA-lipid complexes in contact with the cells. DNA-only/cell and lipid-only/cell control wells were also prepared on one of the three plates.

The 100 μl solutions of DNA-lipid complex were maintained over the cells for 6 hours, after which 50 μl of 30% FBS (in OptiMEM) was added to each well. After a further 20-hour incubation period, an additional 100 μl of 10% FBS in OptiMEM was also added. Following a further 24-hour incubation period, cells were assayed for expression of protein and β-galactosidase.

For the assays, the resultant medium was removed from the plates and the cells washed with phosphate buffered saline. Lysis buffer (50 μl, 250 mM Tris-HCl, pH 8.0, 0.15% Triton X-100) was then added, and the cells were lysed for 30 minutes. The 96-well plates were carefully vortexed for 10 seconds to dislodge the cells and cell debris, and 5 μl volumes of lysate from each well were transferred to a plate containing 100 μl volumes of Coomassie Plus® protein assay reagent (Pierce Company, No. 23236). The protein assay plates were read by a Bio-Rad Model 450 plate-reader containing a 595 nm filter, with a protein standard curve included in every assay.

The level of β-galactosidase activity in each well was measured by adding phosphate buffered saline (50 μl) to the remaining lysates, followed by addition of a buffered solution consisting of chlorophenol red galactopyranoside (100 μl, 1 mg per ml, Calbiochem No. 220588), 60 mM disodium hydrogen phosphate pH 8.0, 1 mM magnesium sulfate, 10 mM potassium chloride, and 50 mM 2-mercaptoethanol. The chlorophenol red galactopyranoside, following enzymatic (β-galactosidase) hydrolysis, gave a red color which was detected by a plate-reader containing a 570 nm filter. A β-galactosidase (Sigma No. G6512) standard curve was included to calibrate every assay.

Following subtraction of background readings, optical data determined by the plate-reader allowed determination of β-galactosidase activity and protein content. In comparison to the amount of β-galactosidase expressed by known transfectants, for example, DMRIE (1,2-dimyristyloxypropyl-3-dimethyl-hydroxyethyl ammonium bromide), compounds of the invention are particularly effective in transfecting airway epithelial cells and inducing therein β-galactosidase expression. Relative to DMRIE:DOPE (1:1), the spermidine cholesterol carbamate:DOPE mixture (also 1:1) demonstrated transfection efficiency improved by a factor of about 5.

Example 2—Transfection of the Gene Encoding for Human Cystic Fibrosis Transmembrane Conductance Regulator Protein The ability of the cationic amphiphiles of the invention to transfect cells and to induce therein biochemical corrections was demonstrated with a separate in vitro assay. Immortalized human cystic fibrosis airway cells (CFT-1, as above) that are homozygous for a mutant allele (deletion of phenylalanine at position 508, hereinafter ΔF508 ) of the gene encoding for cystic fibrosis transmembrane conductance regulator ("CFTR") protein were used. CFTR is a cAMP-regulated chloride ($Cl^-$) channel protein. Mutation of the CFTR gene results typically in complete loss ( or at least substantial impairment) of $Cl^-$ channel activity across, for example, cell membranes of affected epithelial tissues.

The ΔF508 mutation is the most common mutation associated with cystic fibrosis disease. For a discussion of the properties of the ΔF508 mutation and the genetics of cystic fibrosis disease see, in particular, Cheng et al., Cell, 63, 827–834 (1990). See also Riordan et al., Science, 245, 1066–1073 (1989); published European Patent Application No. 91301819.8 of Gregory et al., bearing publication number 0 446 017 A1; and Gregory et al., Nature, 347, 382–385 (1990).

In preparation for the assay, the cells were grown on glass coverslips until approximately 60% confluent. The cells were then transfected with a complex of spermidine cholesterol carbamate:DOPE (1:1) and a plasmid(pCMV-CFTR) containing a cDNA that encodes wild type human CFTR. pCMV-CFTR plasmid is a construct containing the encoding sequence for CFTR and the following regulatory elements, a CMV promoter and enhancer, and an SV40 polyadenylation signal. Additional constructs suitable for the practice of this example include pMT-CFTR, Cheng et al., Cell, 63, 827–834 (1990). The complex used was 10.5 μmolar of spermidine cholesterol carbamate (also of DOPE) and 30 μmolar of pCMV-CFTR based on nucleotide.

48 hours after amphiphile-mediated transfection, cells were tested for cAMP-stimulated $Cl^-$ channel activity using the 6-methoxy-N-(3-sulfopropyl)quinolinium ("SPQ") assay. See S. Cheng et al., Cell, 66, 1027–1036 (1991) for further information concerning assay methodology. In the assay, cAMPdependent $Cl^-$ channel activity was assessed using "SPQ" (from Molecular Probes, Eugene, Oreg.), a halide-sensitive fluorophore. Increases in halide permeability results in a more rapid increase in SPQ fluorescence, and the rate of change (rather than the absolute change in fluorescence) is the important variable in assessing $Cl^-$ permeability. See also Rich et al., Nature, 347, 358–363 (1990) for background information.

Fluorescence of the SPQ molecule in individual cells was measured using an inverted microscope, Nikon, a digital imaging system from Universal Imaging, and an ICCD camera, Hamamatsu, Inc. Cells were selected for analysis without prior knowledge of their expected rate-of-change-in-fluorescence characteristics.

In each experiment, up to five microscope fields of between 90 and 100 cells were examined on a given day, and studies under each condition were repeated on at least 3 different days. Since expression of CFTR is heterogenous (i.e. cells do not produce identical amounts of CFTR), the data presented were for the 20% of cells in each field exhibiting the greatest response.

As expected, cells that were mock transfected failed to exhibit any measurable increase in cAMP-stimulated halide fluorescence. In contrast, cells that had been transfected with the wild type CFTR cDNA displayed a rapid increase in SPQ fluorescence upon stimulation with cAMP agonist, indicating increased permeability to anions. Approximately 60% of the cells assayed exhibited measurable cAMP-stimulated $Cl^-$ channel activity. Accordingly, spermidine cholesterol carbamate, and other cationic amphiphiles of the invention similarly tested, are effective in transferring CFTR-encoding plasmid into immortalized CF airway cells.

Example 3—CAT Assay

This assay was used to assess the ability of the cationic amphiphiles of the invention to transfect cells (in vivo) from live specimens. In the assay, the lungs of balb/c mice were instilled either trans-tracheally or intra-nasally with 100 μl of cationic amphiphile:DNA complex, which was allowed to form during a 15-minute period prior to administration according to the following procedure. The lipid was hydrated in water for 10 minutes, a period sufficient to yield a suspension at twice the final concentration required. This was vortexted for two minutes and aliquoted to provide 55 microliter quantities for each mouse to be instilled. Similarly, DNA encoding the reporter (CAT) gene was diluted with water to a concentration twice the required final concentration, and then aliquoted at 55 microliters for each mouse to be instilled. The lipid was combined with the DNA (in a polystyrene tube) and the complex allowed to form for 15 minutes before the mice were instilled therewith.

The plasmid used (pCMVHI-CAT, see Example 4 below) provides an encoding DNA for chloramphenicol transferase enzyme. Specifics on the amphiphile:DNA complexes are provided below.

Two days following transfection, mice were sacrificed, and the lungs and trachea removed, weighed, and homogenized in a buffer solution (250 mM Tris, pH 7.8, 5 mM EDTA ). The homogenate was clarified by centrifugation, and the deactylases thereof were inactivated by heat treatment at 70° C. for 10 minutes. Lysate was incubated overnight with acetyl coenzyme A and $C^{14}$-chloramphenicol. The presence of the enzyme CAT will cause an acetyl group to be transferred from acetylcoenzyme A to $C^{14}$-chloramphenicol. The acetylated/radiolabeled chloramphenicol migrates faster on a TLC plate and thus its presence can be detected. The amount of CAT that had been necessary to generate the determined amount of acetylated chloramphenicol can then be calculated from standards.

CAT enzyme activity was then visualized by thin layer chromatography ("TLC") following an ethyl acetate extraction. Enzyme activity was quantitated by comparison with a CAT standard curve.

Figure 15:
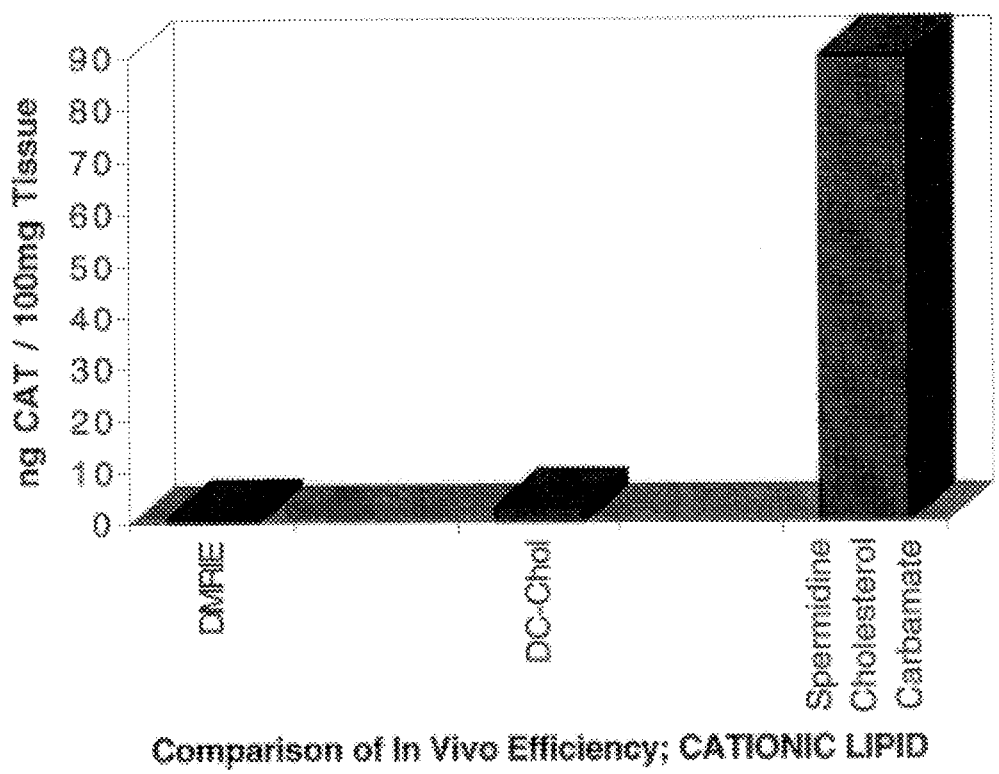
FIG. 15 provides a comparison of in vivo transfection efficiency for certain cationic amphiphiles under particular conditions.

The activity of spermidine cholesterol carbamate was determined in the CAT assay in relation to the recognized transfection reagents DMRIE and to DC-Chol. FIG. 15 demonstrates dramatically (as ng CAT activity per 100 mg tissue) the enhanced ability of spermidine cholesterol carbamate to transfect cells invivo.

With respect to the comparison provided by FIG. 15 the following conditions are of note. The transfection solution for spermidine cholesterol carbamate contained 6 mM pCMVHI-CAT measured as concentration of nucleotide, and 1.5 mM of cationic amphiphile. Following generally the procedure of Example 1, each amphiphile had also been premixed with DOPE, in this case at 1:1 molar ratio. For transfection with DC-chol, the molar ratio of DC-chol to DOPE was 60:40, and the concentrations of cationic amphiphile and of DNA (as nucleotide) were 1.3 mM and 0.9 mM, respectively. For transfection with DMRIE, the molar ratio of DMRIE to DOPE was 1:1 and the concentrations of cationic amphiphile and of DNA were 1.7 mM and 1.2 mM, respectively.

Figure 16:
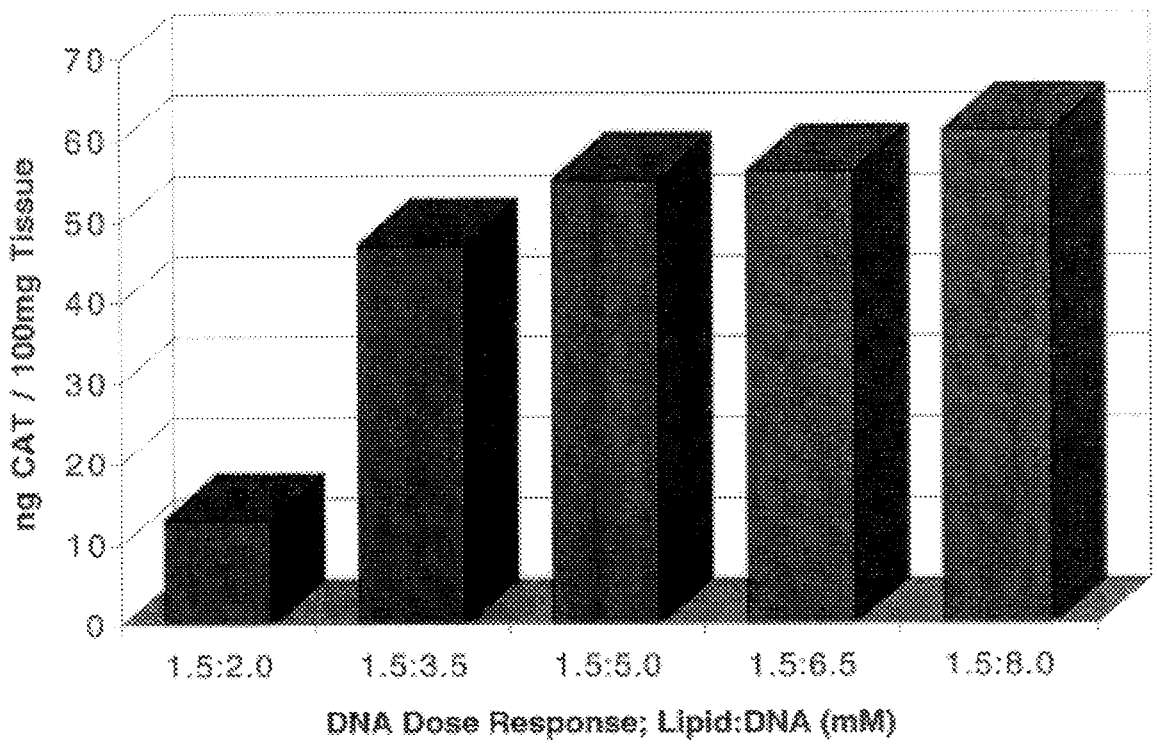
FIG. 16 is a depiction of in vivo transfection efficiency as a function of DNA concentration for a particular cationic amphiphile.
Figure 17:
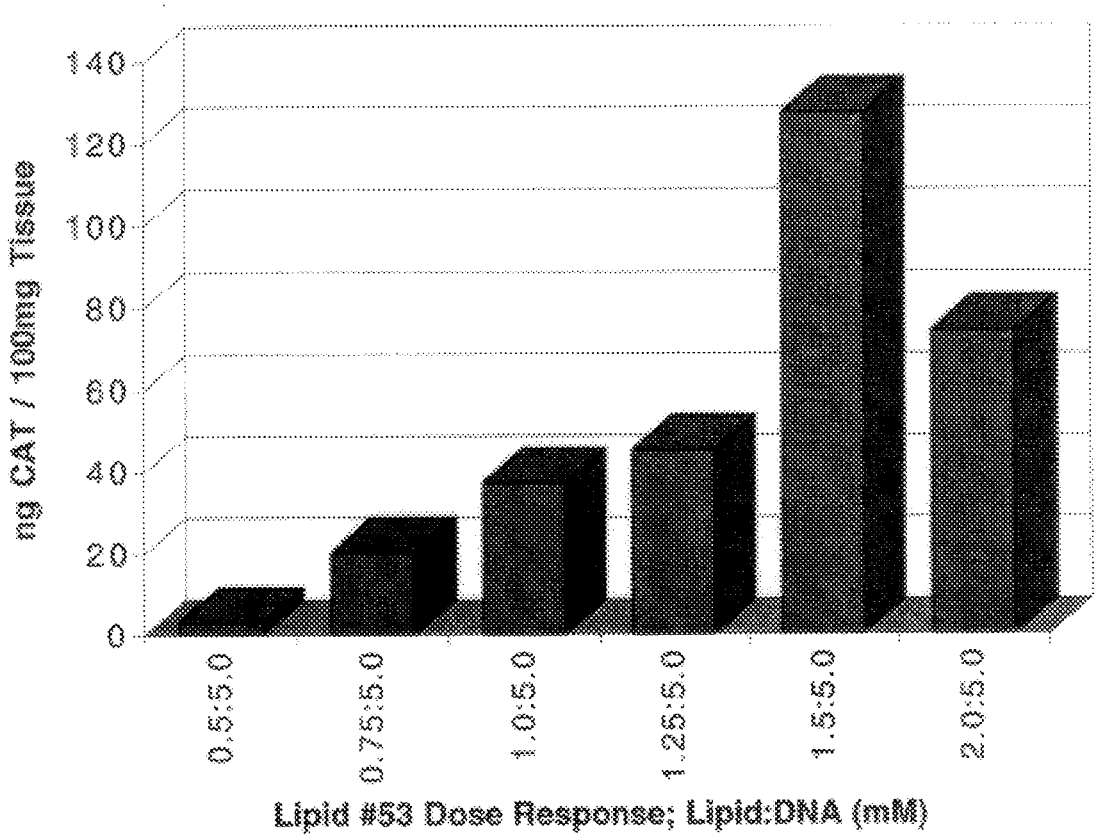
FIG. 17 is a depiction of in vivo transfection efficiency as a function of concentration of a particular cationic amphiphile.
Figure 18:
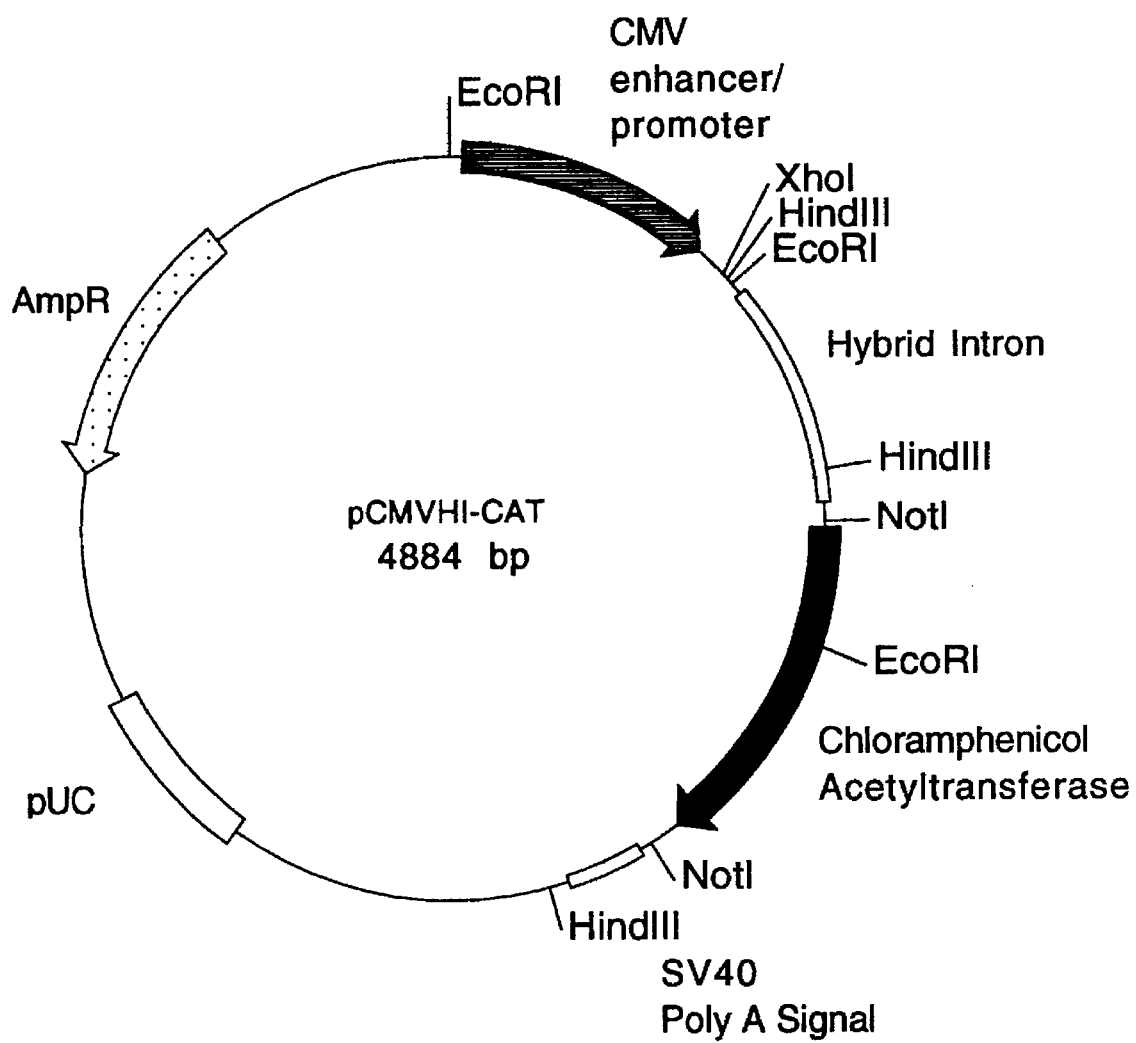
FIG. 18 is a restriction map of pCMVHI-CAT.
Figure 19:
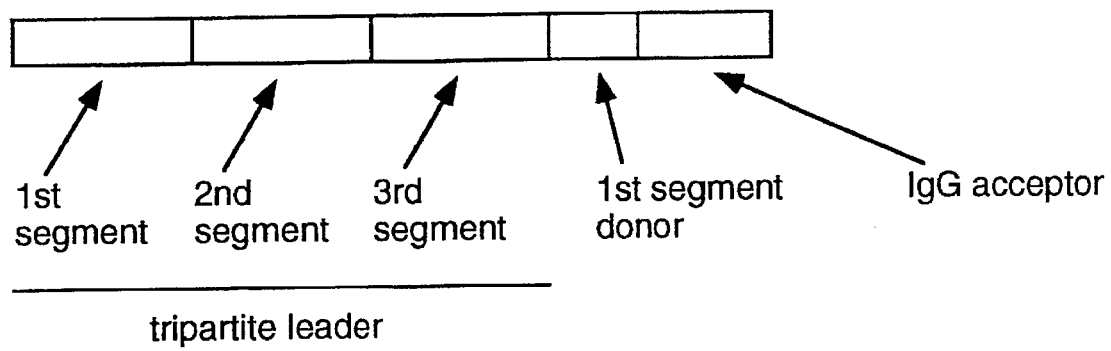
FIG. 19 shows the hybrid intron of pCMVHI-CAT.

For spermidine cholesterol carbamate, optimization experiments were also performed to determine preferred concentrations of plasmid for a particular amphiphile concentration (see FIG. 16), and also to determine preferred concentrations of the same amphiphile in relation to a particular plasmid concentration (see FIG. 17). Transfection effciency was optimal at an amphiphile concentration of 1.5 mM (DOPE also being present at 1.5 mM), and about 5 mM (by nucleotide) of plasmid, or about at a ratio of 1:4. It was noted, however, that concentrations of about 0.75 mM of amphiphile, and 3.0 mM of plasmid were less toxic to the target cells.

Example 4—Construction of pCMVHI-CAT

The vector pCMVβ (Clontech, Palo Alto, Calif.) was digested with Not I to excise the β-galactosidase gene. The vector fragment lacking the β-galactosidase gene was isolated and ligated to form pCMV.

The hybrid intron was obtained from the vector pADβ (Clontech). pADβ was digested with Pml I and Not I, and the ~500 base-pair (bp) fragment was isolated, and then ligated into the Not I site of pBluescriptII KS(-) (Stratagene, La Jolla, Calif.) to form pBlueII-HI.

pBlueII-HI was digested with XhoI and NotI to excise the hybrid intron fragment. This fragment was ligated into the XhoI and NotI sites of pCMV, replacing the SV40 intron to form pCMVHI.

The CAT gene was obtained from the Chloramphenicol Acetyltransferase GertBlock (Pharmacia, Piscataway, N.J.). This 792 bp Hind III fragment was blunted with the Klenow fragment of DNA Polymerase I, then Not I linkers (New England Biolabs) were ligated to each end. After digestion with Not I to expose the Not I sticky ends, the fragment was subcloned into the Not I site of pCMV to form pCMV-CAT. pCMV-CAT was digested with Not I to excise the CAT fragment. The CAT fragment was ligated into pCMVHI to form pCMVHI-CAT.

Example 5—Correction of Chloride Ion Transport Defect in Nasal Polyp Epithelial Cells of a Cystic Fibrosis Patient by Cationic Lipid-Mediated Gene Transfer Primary (non-immortalized) nasal polyp cells from an adult male cystic fibrosis patient (homozygous for the ΔF508mutation) were grown on collagen-coated permeable filter supports (Millicells) to form a polarized and confluent epithelial monolayer. Once the monolayer was electrically tight (about 5 to 7 days post seeding, and as indicated by the development of resistance across the cell sheet), the apical surface can be exposed to formulations of cationic amphiphile: DNA complex.

In this case, the amphiphile (spermidine cholesterol carbamate) was provided as a 1:1 (by mole) mixture with DOPE, and this mixture was then complexed with pCMV-CFTR plasmid vector (a construct encoding wild type human cystic fibrosis transmembrane conductance regulator protein, see above. Concentrations in the final mixture were 42 μmolar of spermidine cholesterol carbamate (and also of DOPE) and 60 μmolar (based on molarity in nucleotides) of the plasmid suspension.

Expression of CFTR was determined by measuring cAMP-stimulated transepithelial chloride secretion in a modified Ussing chamber, Zabnet et al., Nature Genetics, 6, 75–83 (1984). The mucosal side of the epithelium was bathed in Ringer's bicarbonate solution bubbled with 95% $O_2$ and 5% $CO_2$. The composition of the submucosal solution was similar to the mucosal solution with the exception that sodium gluconate replaced sodium chloride. Transepithelial voltage was clamped to 0 mV and short circuit current was recorded. Amiloride (10 μM) was applied into the apical bath, followed by the mucosal addition of forskolin and IBMX (at 100 μM each). 5-nitro-2-(3-phenylpropylamino) benzoic acid ("NPPB"), an inhibitor of CFTR chloride channels, was then added to the mucosal solution at 10 to 30 μM.

Figure 20:
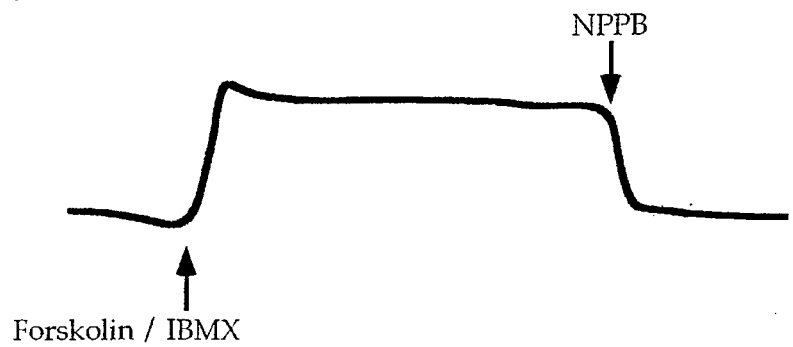
FIG. 20 shows a plot of corrected chloride ion transport in nasal polyp epithelial cells from a cystic fibrosis patient.
Figure 20:
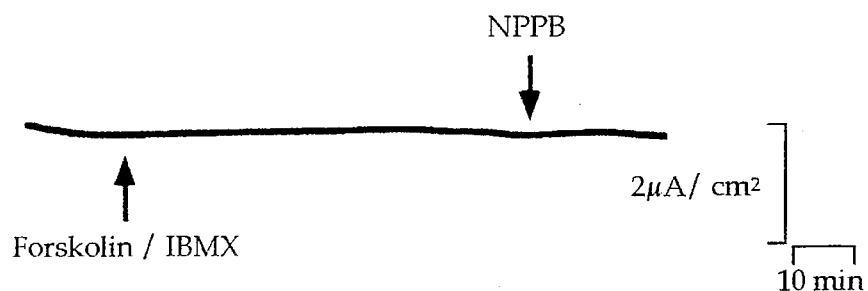

Chloride secretion (i.e. movement of chloride from the epithelial cells to the mucosal solution) is shown as an upward deflection (see FIG. 20). The same plasmid vector, but containing a reporter gene, was used as a negative control. A cAMP-stimulated current (0.5 to 2.5 μampere/cm$^2$) was observed in monolayers transfected with wild type CFTR gene. Current was not detected With the pCMV-β-galactosidase control.

The above descriptions of preferred embodiments of the invention have been presented for purposes of illustration. They are not intended to be exhaustive of or to limit the invention to the precise form disclosed.

We claim:

1. The cationic amphiphile spermidine cholesterol carbamate.

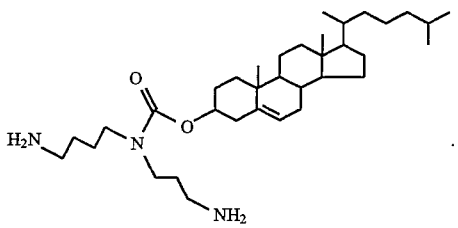

2. A composition comprising the cationic amphiphile of claim 1, and one or more co-lipids selected from the group consisting of lyso-phosphatidylethanolamines, phosphatidylethanolamines, phosphatidylcholines, lyso-phosphatidylcholines, and cholesterol.

3. A composition according to claim 2 wherein the co-lipid is dioleoylphosphatidylethanolamine or diphytanoylphosphatidylethanolamine.

4. A composition according to claim 3 wherein the co-lipid is dioleoylphosphatidylethanolamine and the molar ratio of spermidine cholesterol carbamate to dioleoylphosphatidylethanolamine is 1:1.

5. The cationic amphiphile spermine cholesterol carbamate.

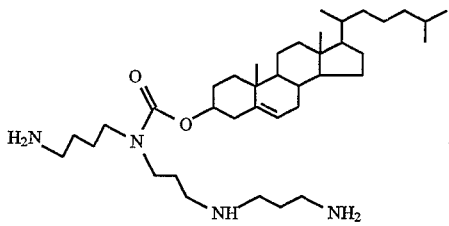

6. A composition comprising the cationic amphiphile of claim 5, and one or more co-lipids selected from the group consisting of lyso-phosphatidylethanolamines, phosphatidylethanolamines, phosphatidylcholines, lyso-phosphatidylcholines, and cholesterol.

7. A composition according to claim 6 wherein the co-lipid is dioleoylphosphatidylethanolamine or diphytanoylphosphatidylethanolamine.

* * * * *

UNITED STATES PATENT AND TRADEMARK OFFICE
CERTIFICATE OF CORRECTION

PATENT NO. : 5,650,096
DATED : July 22, 1997
INVENTOR(S) : HARRIS, David J. et al.

It is certified that error appears in the above-identified patent and that said Letters Patent is hereby corrected as shown below:

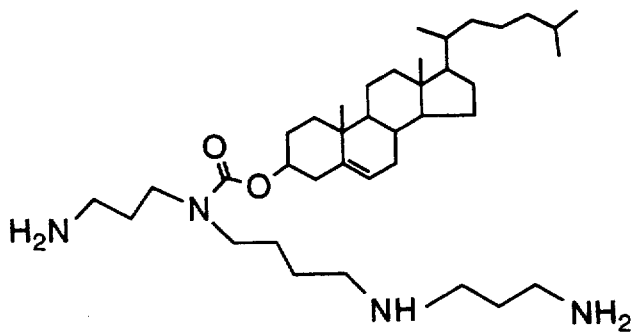

Signed and Sealed this

Thirteenth Day of January, 1998

Attest:

BRUCE LEHMAN

Attesting Officer  Commissioner of Patents and Trademarks